(12) United States Patent
McPherson

(10) Patent No.: US 9,012,735 B1
(45) Date of Patent: Apr. 21, 2015

(54) COTTON VARIETY 98M-2983

(75) Inventor: Mustafa George McPherson, Leland, MS (US)

(73) Assignee: Phytogen Seed Company, Indianapolis, IN (US)

( * ) Notice: Subject to any disclaimer, the term of this patent is extended or adjusted under 35 U.S.C. 154(b) by 1456 days.

(21) Appl. No.: 11/644,331

(22) Filed: Dec. 22, 2006

Related U.S. Application Data

(60) Provisional application No. 60/753,660, filed on Dec. 23, 2005.

(51) Int. Cl.
| | | |
|---|---|---|
| *A01H 1/00* | (2006.01) | |
| *A01H 1/02* | (2006.01) | |
| *A01H 1/04* | (2006.01) | |
| *A01H 1/06* | (2006.01) | |
| *A01H 4/00* | (2006.01) | |
| *A01H 5/00* | (2006.01) | |
| *F16L 23/032* | (2006.01) | |

(52) U.S. Cl.
CPC .................................. *F16L 23/032* (2013.01)

(58) Field of Classification Search
USPC ......... 800/260, 265, 266, 267, 268, 274, 278, 800/279, 314; 435/410
See application file for complete search history.

(56) References Cited

U.S. PATENT DOCUMENTS

| | | | |
|---|---|---|---|
| 5,110,344 A | 5/1992 | Olvey | |
| 5,141,552 A | 8/1992 | Olvey et al. | |
| 6,008,438 A | 12/1999 | Keim | |
| 6,093,876 A * | 7/2000 | Burdett, Jr. | ................... 800/314 |
| 6,102,971 A | 8/2000 | Burdett, Jr. | |
| 2005/0183171 A1 * | 8/2005 | Green et al. | .................. 800/314 |

OTHER PUBLICATIONS

Dow AgroSciences, Risk assessment and risk management plan, DIR 040/2003, Nov. 2003, p. 25, paragraph 115.*
PVP8100029—Curators of the University of Missouri—Nov. 19, 1981.

* cited by examiner

*Primary Examiner* — Shubo (Joe) Zhou
*Assistant Examiner* — Keith Robinson
(74) *Attorney, Agent, or Firm* — C. Philip Poirier; Traskbritt, P.C.

(57) ABSTRACT

A cotton variety, designated 98M-2983, the plants and seeds of the cotton variety 98M-2983, methods for producing a cotton plant, either varietal or hybrid, produced by crossing the cotton variety 98M-2983 with itself or with another cotton plant, and hybrid cotton seeds and plants produced by crossing the variety 98M-2983 with another cotton variety or plant and to methods for producing a cotton plant containing in its genetic material one or more transgenes and to the transgenic cotton plants produced by that method. This invention also relates to cotton varieties derived from cotton variety 98M-2983, to methods for producing other cotton varieties derived from cotton variety 98M-2983 and to the varieties derived by the use of those methods.

74 Claims, No Drawings

COTTON VARIETY 98M-2983

FIELD OF THE INVENTION

This application claims the benefit of U.S. Provisional Application No. 60/753,660, filed on Dec. 23, 2005. This invention is in the field of cotton breeding. In particular, the invention relates to a cotton variety designated 98M-2983 that includes plants and seeds of cotton variety 98M-2983. Methods for producing cotton plants, such as cotton plant varieties, hybrid cotton plants, or other cotton plants, as by crossing cotton variety 98M-2983 with itself or any different cotton plant are an integral part of this invention as are the resultant cotton plants including the plant parts and seeds. This invention further relates to methods for producing 98M-2983-derived cotton plants, to methods for producing male sterile 98M-2983 cotton plants, e.g., cytoplasmic male sterile 98M-2983 cotton plants and to methods for regenerating such plants from tissue cultures of regenerable cells as well as the plants obtained therefrom. Methods for producing a cotton plant containing in its genetic material one or more transgenes and to the transgenic cotton plants produced by that method are also a part of this invention.

BACKGROUND OF THE INVENTION

Cotton (*Gossypium* spp.) is the world's most important textile fiber crop and is one of the world's most important oilseed crops. Cotton plants provide a source of human food, livestock feed, and raw material in industry. Cotton seed is pressed for cooking oil and the residual cottonseed oil meal used for animal feed Industrial uses of cotton include candle wicks, twine, paper and a multitude of fabric products.

The genus *Gossypium* is very large, currently containing more than 50 species. Two tetraploid species of *Gossypium* have spinnable seed fibers called lint. These two species are *G. hirsutum* (referred to as American Upland cotton) and *G. barbadense* (referred to as Pima cotton).

The goal of a cotton breeder is to improve a cotton plant's performance and therefore, its economic value by combining various desirable traits into a single plant. Improved performance is manifested in many ways. Higher yields of cotton plants contribute to a more lint fiber production, a more profitable agriculture and a lower cost of products for the consumer. Improved plant health increases the yield and quality of the plant and reduces the need for application of protective chemicals. Adapting cotton plants to a wider range of production areas achieves improved yield and vegetative growth. Improved plant uniformity enhances the farmer's ability to mechanically harvest cotton.

Cotton is a dicot plant with perfect flowers, i.e., cotton has male, pollen-producing organs and separate female, pollen receiving organs on the same flower. The cultivated cotton flower is surrounded by three triangular bracts forming what is commonly known as squares. The flower contains an open corolla with five petals, a staminal column bearing clusters of stamens and forming a tube that encloses the style. The compound pistil consists of three to five carpels with stigmas protruding above the anthers. The ovary develops into a three- to five-loculed capsule or boll. From seven to nine seeds are set within each lock or locule. On the day preceding anthesis, a twisted corolla emerges from the square. On the day of anthesis, the corolla opens and pollen shedding occurs. The corolla turns red the day following anthesis and later falls from the plant. Pollination occurs with the opening of the anthers and shedding of pollen on the stigma or with the deposit of pollen on the stigma by insects.

Because cotton has both male and female organs on the same flower, cotton breeding techniques take advantage of the plant's ability to be bred by both self-pollination and cross-pollination. Self-pollination occurs when pollen from the male organ is transferred to a female organ on the same flower on the same plant. Self-incompatibility is a form of infertility caused by the failure of cotton plants with normal pollen and ovules to set seed due to some physiological hindrance that prevents fertilization. Self-incompatibility restricts self-pollination and inbreeding and fosters cross-pollination. Cross-pollination occurs when pollen from the male organ on the flower of one plant is transferred to a female organ on the flower on a different plant.

A plant is sib-pollinated (a type of cross-pollination) when individuals within the same family or line are used for pollination (i.e. pollen from a family member plant is transferred to the stigmas of another family member plant). Self-pollination and sib-pollination techniques are traditional forms of inbreeding used to develop new cotton varieties, but other techniques exist to accomplish inbreeding. New cotton varieties are developed by inbreeding heterozygous plants and practicing selection for superior plants for several generations until substantially homozygous plants are obtained. During the inbreeding process with cotton, the vigor of the lines decreases and after a sufficient amount of inbreeding, additional inbreeding merely serves to increase seed of the developed variety. Cotton varieties are typically developed for use in the production of hybrid cotton lines.

Natural, or open pollination, occurs in cotton when bees or other insects transfer pollen from the anthers to the stigmas and may include both self- and cross-pollination. Such pollination is accomplished almost entirely by the bees or other pollinating insects as the pollen is heavy and sticky and accordingly, interplant transfer of pollen by the wind is of little importance. Vigor is restored when two different varieties are cross-pollinated to produce the first generation ($F_1$) progeny. A cross between two defined substantially homozygous cotton plant varieties always produces a uniform population of heterozygous hybrid cotton plants and such hybrid cotton plants are capable of being generated indefinitely from the corresponding variety cotton seed supply.

When two different, unrelated cotton parent plant varieties are crossed to produce an $F_1$ hybrid, one parent variety is designated as the male, or pollen parent, and the other parent variety is designated as the female, or seed parent. Because cotton plants are capable of self-pollination, hybrid seed production requires elimination of or inactivation of pollen produced by the female parent to render the female parent plant male sterile. This serves to prevent the cotton plant variety designated as the female from self-pollinating. Different options exist for controlling male fertility in cotton plants such as physical emasculation, genetic male sterility, cytoplasmic male sterility and application of gametocides. Incomplete removal of male parent plants from a hybrid seed production field before harvest provides the potential for unwanted production of self-pollinated or sib-pollinated seed which may be unintentionally harvested and packaged with hybrid seed.

The development of new cotton plant varieties and hybrid cotton plants is a slow, costly interrelated process that requires the expertise of breeders and many other specialists. The development of new varieties and hybrid cotton plants in a cotton plant breeding program involves numerous steps, including: (1) selection of parent cotton plants (germplasm) for initial breeding crosses; (2) inbreeding of the selected plants from the breeding crosses for several generations to produce a series of varieties, which individually breed true and are highly uniform; and, (3) crossing a selected variety with an unrelated variety to produce the $F_1$ hybrid progeny having restored vigor.

Cotton plant varieties and other sources of cotton germplasm are the foundation material for all cotton breeding programs. Despite the existence and availability of numerous cotton varieties and other source germplasm, a continuing need still exists for the development of improved germplasm because existing parent cotton varieties lose their commercial competitiveness over time. The present invention addresses this need by providing a novel cotton variety designated 98M-2983 that possesses improved bacterial blight resistance together with early maturity and broad adaptation and contributes such characteristics to hybrids relative to other similar hybrids in the same maturity groups. To protect and to enhance yield production, trait technologies and seed treatment options provide additional crop plan flexibility and cost effective control against insects, weeds and diseases, thereby further enhancing the potential of this variety and hybrids with 98M-2983 as a parent.

I. Definitions of Plant Characteristics

In the description and examples that follow, a number of terms are used. To provide a clear and consistent understanding of the specification and claims, including the scope to be given such terms, the following definitions are provided.

Area(s) of Adaptation: This represents whether the cotton plant is adapted (A), not adapted (NA) or not tested (NT) for the following areas: Eastern, Delta, Central, Blacklands, Plains, Western, Arizona, and San Joaquin Valley.

Plant Habit: This represents the general growth habit of the plant rated as spreading, intermediate or compact.

Foliage: This represents the general appearance of the plant leaves rated as sparse, intermediate, or dense.

Stem Lodging: This represents the general appearance of the plant stems relative to their normal near vertical orientation rated as lodging, intermediate, or erect.

Fruiting Branch: This represents fruiting pattern rated as clustered, short, or normal.

Growth: This represents the growing pattern of the cotton plant following a fruiting cycle rated as determinate, i.e., a complete interruption of growth following a fruiting cycle, or indeterminate, i.e., a growth pattern in which stems continue to grow indefinitely.

Leaf Color: This represents a visual assessment of the leaf color of the cotton plant rated as greenish yellow, light green, medium green, dark green.

Boll Shape: This represents the shape of the boll rated as length less than width, length equal to width, or length more than width.

Boll Breadth: This represents a comparison of the boll width at its middle and its base rated as broadest at base, or broadest at middle.

Date of 50% Open Bolls: This represent's the date at which 50% of the bolls of a plant are open.

Maturity (% $1^{st}$ Harvest): This represents the number of open bolls of a plant expressed as a percentage, generally measured about 2 weeks before 100% of the bolls of a plant are open cm to 1st Fruiting Branch: This represents the distance between the cotyledonary node to the first fruiting branch in centimeters.

No. of Nodes to 1st Fruiting Branch: This represents the number of nodes from the cotyledonary node to the first fruiting branch, excluding the cotyledonary node.

Mature Plant Height: This represents the height in centimeters of the cotton plant from the cotyledonary node to terminal.

Leaf Type: This represents the shape of the uppermost fully expanded leaf rated as normal, sub okra, okra, or super okra.

Leaf Pubescence: This represents the density of leaf trichomes ("hairs") on the bottom surface excluding veins of the uppermost fully expanded leaf rated as absent, sparse, medium, or dense in terms of trichomes/$cm^2$.

Leaf Nectaries: This represents whether leaf nectarines are present or absent on the uppermost fully expanded leaf.

Stem Pubescence: This represents whether the stem pubescence is glabrous, intermediate, or hairy.

Leaf Glands: This represents the density of gossypol glands rated as absent, sparse, normal, or more than normal.

Stem Glands: This represents the density of gossypol glands rated as absent, sparse, normal, or more than normal.

Calyx Lobe: This represents the gossypol gland density on the calyx lobe rated as absent (normal), sparse, or more than normal.

Petal Color: This represents a visual assessment of the petal color rated as cream or yellow.

Pollen Color: This represents a visual assessment of pollen color rated as cream or yellow.

Petal Spot: This represents whether petal spot is present or absent on the flowers of the cotton plant.

Seed Index: This represents the weight of 100 seeds in grams on a fuzzy basis.

Lint Index: This represents the weight of lint per 100 seeds in grams.

Lint Percent: This represents the lint (fiber) fraction of seed cotton (lint and seed).

Number of Seeds per Boll: This represents the average number of seeds per boll on the cotton plant.

Grams Seed Cotton per Boll: This represents the average number of grams of seed cotton per boll on the cotton plant.

Boll Type: This represents the boll type rated as stormproof, storm resistant, or open.

Fiber Length: This represents fiber length expressed in hundredths of an inch as measured by High Volume Instrumentation (HVI).

Fiber Uniformity: This represents the uniformity of fiber length in a sample as measured on the HVI, expressed as a percentage.

Fiber Strength: This represents the force required to rupture or to break a bundle of fibers as measured in grams per tex on the HVI.

Fiber Elongation: This represents the amount that a fiver sample will stretch before breakage and is a measure of the deformation of the cotton fiber at rupture expressed as percent change in length based on the original fiber length as measured by HVI.

Fiber Micronaire: This represents a measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly constant and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about 2.0 to 6.0 and have the following meanings: below 2.9 very fine possible small perimeter but mature (good fiber), or large perimeter but immature (bad fiber); from 2.9 to 3.7 fine various degrees of maturity and/or perimeter; 3.8 to 4.6 average degree of maturity and/or perimeter; 4.7 to 5.5 coarse usually fully developed (mature), but larger perimeter; and 5.6 or greater very coarse fully developed, large-perimeter fiber.

Bacterial Blight (Race 1): This represents a visual assessment of the cotton plants for resistance to bacterial blight (race 1) (*Xanthomonas malvacearum*) rated as 0=not tested, 1=susceptible, or 2=moderately susceptible, 3=moderately resistant, or 4=resistant.

II. Cotton Variety 98M-2983

A. Cotton Plant 98M-2983

In accordance with one aspect of the present invention, provided is a new Upland (*Gossypium Hirsutum*) cotton seed and plants thereof designated 98M-2983. The present invention further relates to a method for producing cotton seeds that includes, but is not limited to, the steps of planting seed of cotton variety 98M-2983 in proximity to itself or to different seed from a same family or line, growing the resulting cotton plants under self-pollinating or sib-pollinating conditions with adequate isolation, and harvesting resultant seed obtained from such plants using techniques standard in the agricultural arts such as would be necessary to bulk-up seed such as for hybrid production. The present invention also relates to varietal seed produced by such a method.

In any cross between cotton plant variety 98M-2983 and another cotton plant variety, 98M-2983 may be designated as the male (pollen parent) or the female (seed parent). Optionally, the seed of cotton variety 98M-2983 may be pre-treated to increase resistance of the seed and/or seedlings to stressed conditions, and further, the cotton plants or surrounding soil may be treated with one or more agricultural chemicals before harvest. Such agricultural chemicals may include herbicides, insecticides, pesticides and the like. The present invention also relates to a cotton plant that expresses substantially all of the physiological and morphological characteristics of cotton plant variety 98M-2983 and to a substantially homogenous population of cotton plants having all the physiological and morphological characteristics of cotton plant variety 98M-2983. Any cotton plants produced from cotton plant variety 98M-2983 are contemplated by the present invention and are, therefore, within the scope of this invention. A description of physiological and morphological characteristics of cotton plant 98M-2983 is presented in Table 1.

TABLE 1

| 98-2983 Variety Trait | Value |
| --- | --- |
| AREA(S) OF ADAPTATION | Mid-South, Southeast US |
| PLANT HABIT | Spreading |
| FOLIAGE | Intermediate |
| STEM LODGING | Intermediate |
| FRUITING BRANCH | Normal |
| GROWTH | Intermediate |
| LEAF COLOR | Medium green |
| BOLL SHAPE | Length more than width |
| BOLL BREADTH | Broadest at middle |
| MATURITY (% $1^{st}$ Harvest) | 76.7 |
| CM TO 1ST FRUITING BRANCH | 7.4 |
| NO. OF NODES TO 1ST FRUITING BRANCH | 5.3 |
| MATURE PLANT HEIGHT | 94.7 |
| LEAF TYPE | Normal |
| LEAF PUBESCENCE | Medium |
| LEAF NECTARIES | Present |
| STEM PUBESCENCE | Intermediate |
| LEAF GLANDS | Normal |
| STEM GLANDS | Normal |
| CALYX LOBE | Normal |
| PETAL COLOR | Cream |
| POLLEN COLOR | Cream |
| PETAL SPOT (present or absent) | Absent |
| SEED INDEX (weight of 100 seeds in grams) | 9.3 |
| LINT INDEX (weight of 100 seeds in grams) | 7.3 |
| LINT PERCENT | 44.0 |
| NUMBER OF SEEDS PER BOLL | 30.6 |

TABLE 1-continued

| 98-2983 Variety Trait | Value |
| --- | --- |
| GRAMS SEED COTTON PER BOLL (grams) | 5.1 |
| BOLL TYPE | Open/Loose |
| FIBER LENGTH (hundredths of an inch) | 1.10 |
| FIBER UNIFORMITY (percentage) | 83.9 |
| FIBER STRENGTH (grams per tex) | 30.0 |
| FIBER ELONGATION (percent change) | 7.7 |
| FIBER MICRONAIRE | 4.7 |
| BACTERIAL BLIGHT | R |

It should be appreciated by one having ordinary skill in the art that, for the quantitative characteristics identified in Table 1, the values presented are typical values. These values may vary due to the environment and accordingly, other values that are substantially equivalent are also within the scope of the invention.

Cotton variety 98M-2983 shows uniformity and stability within the limits of environmental influence for the traits described in Table 1. Variety 98M-2983 has been self-pollinated a sufficient number of generations with careful attention paid to uniformity of plant type to ensure the homozygosity and phenotypic stability necessary to use in large scale, commercial production. The line has been increased both by hand and sib-pollinated in isolated fields with continued observations for uniformity. No variant traits have been observed or are expected in 98M-2983.

The present invention also relates to one or more cotton plant parts of cotton plant 98M-2983. Cotton plant parts include plant cells, plant protoplasts, plant cell tissue cultures from which cotton plants can be regenerated, plant DNA, plant calli, plant clumps, and plant cells that are intact in plants or parts of plants, such as embryos, ovules, pollen, stigmas, flowers, petals, seeds, bolls, gossypol glands, stems, leaves, fibers, roots, root tips, and the like.

B. Cotton Seed Designated 98M-2983

A cotton seed is composed of three structural parts: (1) the pericarp, which is a protective outer covering (also known as bran or hull); (2) the germ (also known as an embryo); and (3) the endosperm. Another aspect of the present invention is one or more parts of cotton seed 98M-2983, such as the pericarp of cotton seed 98M-2983 or the germ and/or the endosperm of cotton seed 98M-2983 which remain upon removal of the pericarp and adhering remnants of the seed coat.

Cotton seed designated 98M-2983 may be provided as a substantially homogenous composition of cotton seed designated 98M-2983, that is, a composition that consists essentially of cotton seed 98M-2983. Such a substantially homogenous composition of cotton seed 98M-2983 is substantially free from significant numbers of other varietal and/or hybrid seed so that the varietal seed forms from about 90% to about 100% of the total seed. Preferably, a substantially homogenous composition of the varietal cotton seed contains from about 98.5%, 99%, or 99.5% to about 100% of the varietal seed, as measured by seed grow outs. The substantially homogenous composition of varietal cotton seed of the invention may be separately grown to provide substantially homogenous populations of varietal cotton plants. However, even if a population of varietal cotton plants is present in a field with other different cotton plants, such as in a commercial seed-production field of single-cross hybrid cotton planted in a ratio of 1 male pollinator row to 4 female seed-parent rows, such a population would still be considered to be within the scope of the present invention.

Cotton yield is affected by the conditions to which seeds and seedlings (young plants grown from seeds) are exposed.

Seeds and seedlings may be exposed to one of, or a combination of, for example, cold, drought, salt, heat, pollutants, and disease, all of which are conditions that potentially retard or prevent the growth of crops therefrom. For example, temperature extremes are typical in the upper Midwest region of the United States. Furthermore, diseases evolved from pathogens and deterioration caused by fungi are potentially harmful to seeds and seedlings. Thus, it is desirable to treat seeds as by coating or impregnating the seeds with compositions that render the seeds and seedlings grown therefrom more hardy when exposed to such adverse conditions.

Accordingly, another aspect of the present invention relates to a coated and/or impregnated seed or cotton variety designated 98M-2983 and to coated and/or impregnated seed derived therefrom. Various agents have been used to treat seeds to increase resistance of the plants to stressed conditions, such as cold, drought, salt, and fungi. Such agents include, for example, sodium methylphenyl-pentadienate, trichloroacetic acid, polyoxyalkylene-organo-siloxane block copolymer, 5-aminolevulinic acid, salicylic acid, thiamethoxam, potassium chloride, and polyvinyl alcohol and are useful alone, or in combination in the present invention.

When pre-treating seeds according to the present invention such as before the seeds are planted, the seeds are contacted with the composition of interest, as by coating seeds, spraying seeds, and soaking seeds or a combination thereof, by methods well known to those skilled in the art.

C. Deposit Information.

Applicants have made a deposit of at least 2,500 seeds of cotton variety 98M-2983 with the American Type Culture Collection (ATCC), Manassas, Va. 20110 USA, under ATCC Accession No. PTA-9770. The seeds deposited with the ATCC on Feb. 5, 2009, were taken from a deposit maintained by Phytogen Seed Company since before the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will maintain and will make this deposit available to the public pursuant to the Budapest Treaty.

III. Processes Of Preparing Novel Cotton Plants

A. Novel Cotton Plants Obtained From Variety 98M-2983

Various breeding schemes may be used to produce new cotton varieties from cotton variety 98M-2983. In one method, generally referred to as the pedigree method, 98M-2983 may be crossed with another different cotton plant such as a second parent cotton plant variety, which either itself exhibits one or more selected desirable characteristic(s) or imparts selected desirable characteristic(s) to a hybrid combination. Examples of potentially desired characteristics include greater yield, better stalks, better roots, reduced time to crop maturity, better fiber quality (e.g. fineness, length, length uniformity, strength, reflectance), better storm resistance, better agronomic quality, higher nutritional value, higher starch extractability or starch fermentability, resistance and/or tolerance to insecticides, herbicides, pests, heat and drought, and disease, and uniformity in germination times, stand establishment, growth rate, maturity and boll size. If the two original parent cotton plants do not provide all the desired characteristics, then other sources can be included in the breeding population. Elite varieties can also be used as starting materials for breeding or source populations from which to develop new varieties.

Thereafter, resulting seed is harvested and resulting superior progeny plants are selected and selfed or sib-mated in succeeding generations, such as for about 5 to about 7 or more generations, until a generation is produced that no longer segregates for substantially all factors for which the varietal parents differ, thereby providing a large number of distinct, pure-breeding varieties.

In another embodiment for generating new cotton varieties, generally referred to as backcrossing, one or more desired traits may be introduced into parent cotton plant variety 98M-2983 (the recurrent parent) by crossing the 98M-2983 plants with another cotton plant (referred to as the donor or non-recurrent parent) which carries the gene(s) encoding the particular trait(s) of interest to produce $F_1$ progeny plants. Both dominant and recessive alleles may be transferred by backcrossing. The donor plant may also be a varietal cotton plant, but in the broadest sense can be a member of any plant variety or population cross-fertile with the recurrent parent. Next, $F_1$ progeny plants that have the desired trait are selected. Then, the selected progeny plants are crossed with 98M-2983 to produce backcross progeny plants. Thereafter, backcross progeny plants comprising the desired trait and the physiological and morphological characteristics of cotton variety 98M-2983 are selected. This cycle is repeated for about one to about eight cycles, preferably for about 3 or more times in succession to produce selected higher backcross progeny plants that comprise the desired trait and all of the physiological and morphological characteristics of cotton variety 98M-2983 listed in Table 1 as determined at the 5% significance level when grown in the same environmental conditions. Exemplary desired trait(s) include insect resistance, cytoplasmic male sterility, enhanced fiber quality, enhanced nutritional quality, herbicide resistance, yield stability, yield enhancement, storm resistance, and resistance to bacterial, fungal, nematode and viral disease. One of ordinary skill in the art of plant breeding would appreciate that a breeder uses various methods to help determine which cotton plants should be selected from the segregating populations and ultimately which varieties will be used commercially and will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which varieties and hybrid combinations are significantly better or different for one or more traits of interest. Experimental design methods are used to assess error so that differences between two varieties or two hybrid lines can be more accurately determined. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant, and preferably the traits are measured on plants grown under the same environmental conditions.

This method results in the generation of cotton plants with substantially all of the desired morphological and physiological characteristics of the recurrent parent and the particular transferred trait(s) of interest. Because such cotton plants are heterozygous for loci controlling the transferred trait(s) of interest, the last backcross generation would subsequently be selfed to provide pure breeding progeny for the transferred trait(s).

Backcrossing may be accelerated by the use of genetic markers such as SSR, RFLP, SNP or AFLP markers to identify plants with the greatest genetic complement from the recurrent parent.

Direct selection may be applied where a single locus acts as a dominant trait, such as the herbicide resistance trait. For this selection process, the progeny of the initial cross are sprayed with the herbicide before the backcrossing. The spraying eliminates any plants which do not have the desired herbicide resistance characteristic, and only those plants which have the herbicide resistance gene are used in the subsequent backcross. In the instance where the characteristic being transferred is a recessive allele, it may be necessary to introduce a test of the progeny to determine if the desired characteristic has been successfully transferred. The process of selection, whether direct or indirect, is then repeated for all additional backcross generations.

It should be appreciated by those having ordinary skill in the art that backcrossing can be combined with pedigree breeding as where variety 98M-2983 is crossed with another cotton plant, the resultant progeny are crossed back to variety 98M-2983 and thereafter, the resulting progeny of this single backcross are subsequently inbred to develop new varieties. This combination of backcrossing and pedigree breeding is useful as when recovery of fewer than all of the 98M-2983 characteristics than would be obtained by a conventional backcross are desired.

In an additional embodiment of the present invention, new cotton varieties can be developed by a method generally referred to as haploid breeding. In this methodology, haploid plants are generated from diploid, heterozygous cotton plants that result from crossing cotton plant variety 98M-2983 with another, different cotton plant. Such haploid cotton plants may be generated by methods known to those skilled in the art such as by culturing haploid anthers or embryos from a diploid plant. Alternately, such haploid cotton plant may be generated by crossing the diploid heterozygous cotton plant with a cotton plant that comprises a haploid inducing gene which, when present in the female parent results in offspring with a greatly enhanced frequency of haploids of both maternal and paternal origin. Thereafter, homozygous diploid plants are produced by the doubling of a set of chromosomes (1N) from a haploid plant generated by self-pollination such as through use of a doubling agent, such as colchicine, nitrous oxide gas, heat treatment and trifluralin. The technique of haploid breeding is advantageous because no subsequent inbreeding is required to obtain a homozygous plant from a heterozygous source. Thus, in another aspect of this invention a new cotton plant variety is developed by a method that includes the steps of crossing 98M-2983 or a hybrid made with 98M-2983 with another cotton plant having a propensity to generate haploids to produce haploid progeny plants, and selecting desirable cotton plants from the haploid progeny plants.

The present invention also relates to novel cotton plants produced by a method generally referred to as mutation breeding whereby one or more new traits may be artificially introduced into cotton variety 98M-2983. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis and selected, the trait may then be incorporated into existing germplasm by traditional breeding techniques. Details of mutation breeding can be found in "Principals of Cultivar Development" Fehr, 1993 Macmillan Publishing Company the disclosure of which is incorporated herein by reference.

The mutagenesis treatment may be applied to various stages of plant development, including but not limited to cell cultures, embryos, microspores and shoot apices as well as to cotton seeds. By way of example, pollen may be mixed with a solution of 1 ml EMS and 100 mls Fisher paraffin oil (stock diluted by 1 ml and 15 mls oil solution) every minute for the first 5 minutes and then every five minutes for 45 minutes to keep the pollen suspended. Thereafter, the pollen/paraffin oil solution is brushed onto the stigmas of emasculated flower buds. A paper soda straw is used to cover the stigma to prevent contamination. The cotton boll is picked at maturity and then resultant seeds or the plants therefrom are screened for the desired mutant trait(s).

Once new varieties created, the next step is to determine if the new varieties have any value. This is accomplished by techniques of measuring the combining ability of the new varietal plant, as well as the performance of the variety itself. Combining ability refers to a variety's contribution as a parent when crossed with other varieties to form hybrids. Specific combining ability (SCA) refers to the ability of a variety to cross to another specific variety to form a hybrid. General combining ability (GCA) refers to the ability of a variety to cross to a wide range of varieties to form hybrids. The methodology of forming hybrids to evaluate a variety's contribution as a parent for the purpose of selecting superior varieties is interchangeably known as experimental, top or test crossing.

B. Novel Varieties Obtained from a Hybrid Having Variety 98M-2983 as a Parent

In accordance with processes of the present invention, a hybrid plant having variety 98M-2983 as a parent is crossed with itself or any different cotton plant such as a varietal cotton plant or a hybrid cotton plant to develop a novel variety. For example, a hybrid cotton plant having cotton plant variety 98M-2983 as a parent may be inbred, i.e., crossed to itself or sib-pollinated, and the resulting progeny each selfed for about 5 to about 7 or more generations, thereby providing a set of distinct, relatively pure-breeding varieties wherein each of the varieties received all of its alleles from the hybrid cotton plant having cotton plant variety 98M-2983 as a parent. Double haploid methods can also be used to obtain a cotton plant variety that is homozygous at essentially every locus, wherein the cotton plant variety received all of its alleles from the hybrid cotton plant having cotton plant 98M-2983 as a parent. In other embodiments, a hybrid cotton plant having cotton plant variety 98M-2983 as a parent is crossed with a different cotton plant that may include any varietal cotton plant that is not varietal cotton plant 98M-2983, any hybrid cotton plant that does not have 98M-2983 as a parent, another germplasm source, a haploid or mutation inducing stock, or a trait donor plant, thereby providing a set of distinct, relatively pure-breeding varieties. The resulting varieties could then be crossed with other varieties or other cotton germplasm and the resulting progeny analyzed for beneficial characteristics. In this way, novel varieties conferring desirable characteristics could be identified.

C. "Chasing Selfs"

In the event that commercial cotton hybrids are developed, both female and male varietal seed may occasionally be found within a commercial bag of hybrid seed. Chasing the selfs involves identifying parental varietal plants within a stand of cotton that has been grown from a bag of hybrid cotton seed. Once the seed is planted, the parental plants may be identified and selected due to their variance from the population norm, i.e., by their stature, fruiting branch structure, leaf shape, leaf pubescence, fiber quality traits, or yield components relative to the hybrid plants that grow from the hybrid seed which predominates in a commercial bag of hybrid seed. By locating the parental plants, isolating them from the rest of the plants, and self-pollinating them (i.e., "chasing selfs"), a breeder can obtain a variety that is identical to a parent used to produce the hybrid.

Accordingly, another embodiment of the present invention is directed to a method for producing cotton plant variety 98M-2983 comprising: (a) planting a collection of seed, such as a collection of seed comprising seed of a hybrid, one of whose parents is cotton plant variety 98M-2983, the collection also comprising seed of the variety; (b) growing plants from said collection of seed; (c) identifying parent plants; (d) controlling pollination in a manner which preserves substantial homozygosity of the parent plant; and, (e) harvesting resultant seed. Step (c) may further comprise identifying plants with decreased vigor, i.e., plants that appear less robust than the other plants, or identifying plants that have a genetic profile in accordance with the genetic profile of 98M-2983, such as an SSR genetic profile in accordance with Table 5 herein. Cotton plants capable of expressing substantially all of the physiological and morphological characteristics of cotton variety 98M-2983 include cotton plants obtained by chasing selfs from a bag of hybrid seed.

One having skill in the art will recognize that once a breeder has obtained cotton variety 98M-2983 by chasing selfs from a bag of hybrid seed, the breeder can then produce new varietal plants such as by sib-pollinating, i.e., crossing the cotton plant 98M-2983 with another cotton plant 98M-2983, or by crossing the cotton plant 98M-2983 with a hybrid cotton plant obtained by growing the collection of seed.

IV. Novel Hybrid Plants

A. Novel Hybrid Seeds and Plants

In yet another aspect of the invention, processes are provided for producing cotton seeds or plants, which processes generally comprise crossing a first parent cotton plant with a second parent cotton plant wherein at least one of the first parent cotton plant or the second parent cotton plant is parent cotton plant variety 98M-2983. In some embodiments of the present invention, the first cotton plant variety is 98M-2983 and is a female and in other embodiments the first cotton plant variety is 98M-2983 and is a male. These processes may be further exemplified as processes for preparing hybrid cotton seed or plants, wherein a first cotton plant variety is crossed with a second cotton plant of a different, distinct variety to provide a hybrid that has, as one of its parents, the cotton plant variety 98M-2983. In this case, a second variety is selected which confers desirable characteristics when in hybrid combination with the first variety. In these processes, crossing will result in the production of seed and lint. The seed and lint production occurs regardless whether the seed and/or lint is collected.

Any time the cotton plant variety 98M-2983 is crossed with another, different cotton variety, a first generation ($F_1$) cotton hybrid plant is produced. As such, an $F_1$ hybrid cotton plant may be produced by crossing 98M-2983 with any second cotton plant variety. Therefore, any $F_1$ hybrid cotton plant or cotton seed which is produced with 98M-2983 as a parent is part of the present invention.

When cotton plant variety 98M-2983 is crossed with another cotton plant variety to yield a hybrid, the original variety can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because of increased seed and/or lint yield and preferred production characteristics, such as optimal seed size and quality or ease of boll or lint removal. Particularly in very hot climates, such as in the Southwest USA, pollen can shed better by one plant, thus rendering that plant as the preferred male parent. It is generally preferable to use 98M-2983 as the male parent.

In embodiments of the present invention, the first step of "crossing" the first and the second parent cotton plants comprises planting, preferably in pollinating proximity, seeds of a first cotton plant variety and a second, distinct cotton plant variety. As discussed herein, the seeds of the first cotton plant variety and/or the second cotton plant variety can be treated with compositions that render the seeds and seedlings grown therefrom more hardy when exposed to adverse conditions.

A further step comprises cultivating or growing the seeds of the first and second parent cotton plants into plants that bear flowers. If the parental plants differ in timing of sexual maturity, techniques may be employed to obtain an appropriate nick, i.e., to ensure the availability of pollen from the parent cotton plant designated the male during the time at which stigmas on the parent cotton plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth.

In a preferred embodiment, the cotton plants are treated with one or more agricultural chemicals as considered appropriate by the grower.

A subsequent step comprises preventing self-pollination or sib-pollination of the plants, i.e., preventing the stigmas of a plant from being fertilized by any plant of the same variety, including the same plant. This is preferably done in large scale production by controlling the male fertility, e.g., treating the flowers so as to prevent pollen production or alternatively, using as the female parent a male sterile plant of the first or second parent cotton plant (i.e., treating or manipulating the flowers so as to prevent pollen production, to produce an emasculated parent cotton plant or using as a female, a cytoplasmic male sterile version of the cotton plant). This control may also be accomplished in small scale production by physical removal of the staminal column of individual flowers before anthesis to provide effective control of unwanted self-pollination or sib-pollination.

Yet another step comprises allowing cross-pollination to occur between the first and second parent cotton plants. When the plants are not in pollinating proximity, this is done by either collecting ripe, undehisced anthers from a flower on the pollen parent with a short section of a soda straw during the same evening of the emasculations, or collecting whole, freshly dehisced flowers during the next morning after the emasculations. The soda straw containing the ripe anthers is then slipped over the stigma of an emasculated flower. Finally, bracts are wired around the soda straw, holding it in place over the style, thus protecting the stigma from foreign pollen. If a whole flower from the male parent is used, the petals are folded down and the staminal column is rubbed onto the emasculated stigma. In small scale production, seeds of hybrid cotton are commercially produced by hand emasculation and pollination, or by hand pollination of genetic male-sterile cotton. In large scale production, seed of hybrid cotton are commercially produced by using various bee and other insect pollinators to cross pollinate genetic or cytoplasmic male-sterile cotton, or cotton that has been treated with a chemical that results in male sterility.

A further step comprises harvesting the seeds and/or lint, near or at maturity, from the bolls of the plants that received the pollen. In a particular embodiment, seed and/or lint is harvested from the female parent plant, and when desired, the harvested seed can be grown to produce a first generation ($F_1$) hybrid cotton plant.

Yet another step comprises ginning the seed cotton to separate the seed from the marketable lint and delinting the "fuzzy" seed to remove the short "linters" that remain attached after ginning. The seed are further conditioned and treated with chemicals such as fungicides and insecticides prior to being packaged for sale to growers for the production of lint and seed. As with varietal seed, it may be desirable to treat hybrid seeds with compositions that render the seeds and seedlings grown therefrom more hardy when exposed to adverse conditions. Mention should be made that resulting hybrid seed is sold to growers for the production of seed and lint and not generally for breeding.

Still further, the present invention provides a hybrid cotton plant produced by growing the harvested seeds produced on the male-sterile plant as well as seed produced by the hybrid cotton plant.

A single cross hybrid is produced when two different parent cotton plant varieties are crossed to produce first generation $F_1$ hybrid progeny. Generally, each parent cotton plant variety has a genotype which complements the genotype of the other parent variety. Typically, the $F_1$ progeny are more vigorous than the respective parent cotton plant varieties. This hybrid vigor, or heterosis, is manifested in many polygenic traits, including markedly improved yields and improved fruiting, roots, uniformity and insect and disease resistance. It is for this reason that single cross $F_1$ hybrids are generally the most sought after hybrid. A three-way, or modified single-cross hybrid is produced from three varieties where two of the varieties are crossed (A×B) and then the resulting $F_1$ hybrid is crossed with the third variety (A×B)×C, as where a modified female is used in the cross. A modified female provides an advantage of improved seed/lint parent yield whereas a modified male improves pollen flow. A double cross hybrid is produced from four varieties crossed in pairs (A×B and C×D), thereby resulting in two $F_1$ hybrids that are crossed again. Double cross hybrids are more common in countries wherein less demand exists for higher yielding single cross hybrids. Synthetic populations or crosses are developed by crossing two or more varieties (or hybrids, or germplasm sources) together and then employing one of many possible techniques to random mate the progeny. Random mating the progeny is any process used by plant breeders to make a series of crosses that will create a new germplasm pool from which new breeding germplasm can be derived. Since cross pollination of male sterile cotton plants by hand or by various insects is generally very inefficient, $F_1$ hybrid seed is generally too expensive to produce on a large scale. Consequently, the $F_2$ seed harvested from $F_1$ hybrids may retain suitable heterosis to be an economically viable option to pure-line varieties.

The utility of the cotton plant variety 98M-2983 also extents to crosses with species other than the *hirsutum* species, such as *barbadense*. Commonly, suitable species will be of the family Malvaceae, and especially of the genera *Gossypium*.

B. Cotton Varietal Comparison

As mentioned above, experimental strains are progressively eliminated following detailed evaluations of their phenotype, including formal comparisons with other commercially successful varieties. Research small-plot trials and commercial strip trials are used to compare the phenotypes of varieties grown in as many environments as possible. They are performed in many environments to assess overall performance of the new varieties and to select optimum growing conditions. Because the cotton strains and varieties are grown in close proximity, differential effects of environmental factors that affect gene expression, such as moisture, temperature, sunlight, and pests, are minimized. For a decision to be made to advance a strain, it is not necessary that the strain be better than all other varieties. Rather, significant improvements must be shown in at least some traits that would create value for some applications or markets. Some experimental strains are eliminated despite being similarly competitive relative to the current commercial varieties because of the cost to bring a new variety to market requires a new product to be a significant improvement over the existing product offering. Such varieties may also be licensed to other parties who have a need in their commercial product portfolio.

The results in Table 2 show comparative data for different cotton varieties Phytogen PSC355 and Stoneville Pedigreed Seeds ST474.

TABLE 2

| | Value | |
| --- | --- | --- |
| Variety Trait | PSC355 | ST474 |
| AREA(S) OF ADAPTATION | Mid-South, Southeast US | Mid-South, Southeast US |
| PLANT HABIT | Intermediate | Intermediate |
| FOLIAGE | Intermediate | Intermediate |
| STEM LODGING | Erect | Erect |
| FRUITING BRANCH | Short | Short |
| GROWTH | Intermediate | Intermediate |
| LEAF COLOR | Greenish yellow | Light green |
| BOLL SHAPE | Length more than width | Length more than width |
| BOLL BREADTH | Broadest at middle | Broadest at middle |
| MATURITY (% 1st Harvest) | 77.3 | 76.8 |
| CM TO 1ST FRUITING BRANCH | 6.4 | 8.3 |
| NO. OF NODES TO 1ST FRUITING BRANCH | 5.0 | 6.3 |
| MATURE PLANT HEIGHT | 94.6 | 85.2 |
| LEAF TYPE | Normal | Normal |
| LEAF PUBESCENCE | Dense | Dense |
| LEAF NECTARIES | Present | Present |
| STEM PUBESCENCE | Hairy | Hairy |
| LEAF GLANDS | Normal | Normal |
| STEM GLANDS | Normal | Normal |
| CALYX LOBE | Normal | Normal |
| PETAL COLOR | Cream | Cream |
| POLLEN COLOR | Cream | Cream |
| PETAL SPOT (present or absent) | Absent | Absent |
| SEED INDEX (weight of 100 seeds in grams) | 9.7 | 9.6 |

TABLE 2-continued

| Variety Trait | Value | |
| --- | --- | --- |
| | PSC355 | ST474 |
| LINT INDEX (weight of 100 seeds in grams) | 6.9 | 7.2 |
| LINT PERCENT | 41.4 | 42.8 |
| NUMBER OF SEEDS PER BOLL | 30.6 | 28.8 |
| GRAMS SEED COTTON PER BOLL (grams) | 5.1 | 4.8 |
| BOLL TYPE | Open/Loose | Open |
| FIBER LENGTH (hundredths of an inch) | 1.10 | 1.09 |
| FIBER UNIFORMITY (percentage) | 83.9 | 84.0 |
| FIBER STRENGTH (grams per tex) | 30.0 | 29.6 |
| FIBER ELONGATION (percent change) | 7.7 | 7.4 |
| FIBER MICRONAIRE | 4.7 | 4.9 |
| BACTERIAL BLIGHT | S | — |

V. Novel 98M-2983-Derived Plants

All plants produced using cotton plant variety 98M-2983 as a parent are within the scope of this invention, including plants derived from cotton plant variety 98M-2983. This includes plants essentially derived from variety 98M-2983 with the term "essentially derived variety" having the meaning ascribed to such term in 7 U.S.C. §2104(a)(3) of the Plant Variety Protection Act, which definition is hereby incorporated by reference. This also includes progeny plant and parts thereof with at least one ancestor that is cotton plant variety 98M-2983 and more specifically where the pedigree of this progeny includes 1, 2, 3, 4, and/or 5 or cross pollinations to cotton plant 98M-2983, or a plant that has 98M-2983 as a progenitor. All breeders of ordinary skill in the art maintain pedigree records of their breeding programs. These pedigree records contain a detailed description of the breeding process, including a listing of all parental lines used in the breeding process and information on how such line was used. Thus, a breeder would know if 98M-2983 were used in the development of a progeny line, and would also know how many breeding crosses to a line other than 98M-2983 were made in the development of any progeny line. A progeny line so developed may then be used in crosses with other, different, cotton varieties to produce first generation F1 cotton hybrid seeds and plants with superior characteristics.

Accordingly, another aspect of the present invention is methods for producing a 98M-2983-derived cotton plant. This method for producing a 98M-2983-derived cotton plant, comprises: (a) crossing cotton plant 98M-2983 with a second cotton plant to yield progeny cotton seed; and, (b) growing the progeny cotton seed, (under plant growth conditions), to yield the 98M-2983-derived cotton plant. Such methods may further comprise the steps of: (c) crossing the 98M-2983-derived cotton plant with itself or another cotton plant to yield additional 98M-2983-derived progeny cotton seed; (d) growing the progeny cotton seed of step (b) (under plant growing conditions), to yield additional 98M-2983-derived cotton plants; and (e) repeating the crossing and growing steps of (c) and (d) from 0 to 7 times to generate further 98M-2983-derived cotton plants. Still further, this may comprise utilizing methods of semigamy and other haploid breeding and plant tissue culture methods to derive progeny of the 98M-2983-derived cotton plant.

VI. Tissue Cultures and in Vitro Regeneration of Cotton Plants

As is well known in this art, tissue culture of cotton may be used for the in vitro regeneration of a cotton plant. Accordingly, a further aspect of the invention relates to tissue cultures of the cotton plant variety designated 98M-2983, to tissue cultures of hybrid and derived cotton plants obtained from 98M-2983, to plants obtained from such tissue cultures and to the use of tissue culture methodology in plant breeding. The term "tissue culture" includes a composition comprising isolated cells of the same type, isolated cells of a different type, or a collection of such cells organized into parts of a plant. Exemplary tissue cultures are protoplasts, calli and plant cells that are intact in plants or parts of plants, such as embryos, pollen, ovules, flowers, petals, seeds, bolls, gossypol glands, stems, leaves, fibers, roots, root tips, and the like. In a preferred embodiment, the tissue culture comprises embryos, protoplasts, meristematic cells, pollen, leaves or anthers derived from immature tissues of these plant parts.

A. Cotyledon Culture

To obtain for callus culture initiation, seeds are harvested from a wild type cotton plant (generally GC510 or Coker310 genotype). Initially, seeds are surface sterilized by a triple rinse with 70% ethanol for 1 minute each, a thorough rinse with sterile water, followed by a wash in 30% commercial bleach (0.1% sodium hypochlorite) for about 20 minutes.

Seeds are rinsed in sterile distilled water, and seeds are placed on the surface of germination media (LS salts (10×), 3% sucrose, modified B5 vitamins (1000×), at pH 5.8) for the production of sterile plantlets. Approximately, 7-10 days post plating plantlets will have emerged from the seeds. The "first true leaves" are the cotyledons. Generally, tissue culture media contains amino acids, salts, sugars, hormones, and vitamins. The proportion of one ingredient versus another depends on the application (e.g., need for rooting versus shoot elongation). At day 7-10, the cotyledons are of sufficient size for experiment use. The cotyledons are cut into 1 mm square pieces and plated on callus induction media (100 ml/L LS salts (10×), 3% glucose, 1 ml/L modified B5 vitamins (1000×), 1 ml/L 1 mM kinetin, 1 ml/L 1 mM 2,4-D, 8 g/L noble agar, pH 5.8). The cotyledon segment is placed on the media in the abaxial side down orientation. After three weeks on the callus induction media, callus forms around the cut edges of the segment; the callus is removed from the edges using a scalpel. The "callus" is a loose collection or mass of undifferentiated cells—it can be yellow-green in color-some lines are prone to phenolic production (browning) which can effect growth. The callus is maintained on the initiation media for nine weeks, with subculture to fresh media every three weeks. If the segments are treated with *Agrobacterium*, the callus induction media would include carbenecillin, an antibiotic to kill the *Agrobacterium* (2 ml/L), and glufosinate-ammonium is the selective agent that would allow growth of only those cells that contain the transgene (PAT) (0.5 ml/L).

At week nine, the callus is transferred to a growth media (100 ml/L LS salts, 3% glucose, 1 ml/L B5 vitamins, 4.6 ml/L kinetin, 10.7 ml/L NAA, 8 g/L noble agar, pH 5.8), if *Agrobacterium* infection was used to transfer the PAT gene, carbenecillin (0.4 ml/L) and glufosinate ammonium (0.3 ml/L). The callus should remain on this media for 3 weeks, to allow for increased growth before going to embryogenic callus induction media. Once you have sufficient callus, place the tissue on embryogenic induction media (1 pkg DKW salts, 10 ml/L myo-inositol, 1 ml/L B5 vitamins, 2% glucose, 8 g/L noble agar, pH 5.8). The time for a line to produce embryogenic callus varies, it can take two to six months, during this time the callus remains on the same plate of media. Stress can assist in inducing cotton callus to become embryogenic.

Regeneration begins with embryogenic callus. Embryogenic callus is maintained on the embryogenic callus induction media with two week subcultures to fresh media. Microscope use is preferred for the isolation and transfer of embryogenic callus to ensure the desired morphology is taken from the plates. The desired morphology has a granular appearance, the round balls are yellow-green color. The embryogenic callus will give rise to embryos, which may look like small footballs, which have more of a green color. The embryos mature on the embryogenic callus induction media. It may take three to nine weeks for the embryos to mature or elongate, transfers occur at three week intervals. At this stage the embryos are transferred to a basal media that will improve shoot (1 pkg DKW salts, 10 ml/L myo-inositol, 1 ml/L modified B5 vitamins, 3% sucrose, 0.5 ml/L kinetin, 8 g/L noble agar, pH 5.8) or root development (0.5 pkg DKW salts, 5 m/L myo-inositol, 0.5 ml/L modified B5 vitamins, 1% sucrose, 8 g/L noble agar, pH5.8).

When secondary roots have formed and the shoot is 1-2 inches with two good leaves, the cotton plant is ready for soil. Plantlets are first placed in a conviron in small pots with a humidi-dome to assist with plant hardening, since cotton plants can be quite fragile. Then plants are later transferred to large pots in the greenhouse. Most cotton plants are allowed to self-pollinate and these flowers are tagged with one color, while others may be crossed with an elite variety and tagged separately.

B. Additional Tissue Cultures and Regeneration

Other means for preparing and maintaining plant tissue cultures are well known in the art. By way of example, reference may be had to Komatsuda, T. et al., Crop Sci. 31:333-337 (1991); Stephens, P. A., et al., Theor. Appl. Genet. 82:633-635 (1991); Komatsuda, T. et al., Plant Cell, Tissue and Organ Culture, 28:103-113 (1992); Dhir, S. et al. Plant Cell Reports 11:285-289 (1992); Pandey, P. et al., Japan J. Breed. 42:1-5 (1992); and Shetty, K., et al., Plant Science 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce cotton plants having the physiological and morphological characteristics of the present cotton variety.

VII. Male Sterility

Methods for controlling male fertility in cotton plants offer the opportunity for improved plant breeding, particularly for the development of cotton hybrids which require the implementation of a male sterility system to prevent the varietal parent plants from self-pollination.

Accordingly, another aspect of the present invention is male-sterile varietal cotton plants designated 98M-2983 and the production of hybrid cotton seed using a male sterility system with such varietal female parent plants that are male sterile. In the event that cotton variety 98M-2983 is employed as the female parent, 98M-2983 can be rendered male-sterile by, for example, removing the stamens of 98M-2983 parental plants manually. By way of example, alternate strips of two cotton varieties may be planted in a field followed by manual emasculation. Provided that the female variety is sufficiently isolated from foreign cotton pollen sources, the stigma of the emasculated variety will be fertilized only from the other male variety either manually or by insect pollinator vectors, and the resulting seed will therefore be hybrid seed.

The laborious and occasionally unreliable manual emasculation process can be minimized by using cytoplasmic male-sterile (CMS) varieties. Plants of a CMS variety are male sterile as a result of factors resulting from cytoplasmic as opposed to the nuclear genome. Thus, this characteristic is inherited exclusively through the female parent in cotton plants since CMS plants are fertilized with pollen from another variety that is not male-sterile. Pollen from the second variety may or may not contribute genes that make the hybrid plants male-fertile. Seed from emasculated fertile cotton and CMS produced seed of the same hybrid can be blended to insure that adequate pollen loads are available for fertilization when the hybrid plants are grown. Conventional backcrossing methodology may be used to introgress the CMS trait into variety 98M-2983.

Alternatively, haploid breeding methods may also be employed to convert variety 98M-2983 to CMS sterility. Haploids are plants which contain only one-half of the chromosome number present in diploid somatic cells, which are cells other than haploid cells such as those found in the germ. There are a few stocks or genetic systems in cotton which are known to generate haploids spontaneously.

Manual emasculation can also be avoided by the use of chemically induced male sterility in the production of hybrid cotton seed. Chemicals that induce male sterility include gametocides, pollen suppressants, and chemical hybridizing agents. The general procedure is to use a foliar spray before flowering, which inhibits production of viable pollen, but does not injure the pistillate reproductive organs or affect seed development. If the treatment is successful and all of the pollen killed, self-pollination will not occur in the treated plants, but the flowers will set seed freely from cross-pollination. In such a case, the parent plants used as the male may either not be treated with the chemical agent or may include a genetic factor which causes resistance to the sterilizing effects of the chemical agent. The use of chemically induced male sterility affects fertility in the plants only for the growing season in which the gametocide is applied.

The presence of a male-fertility restorer gene results in the production of a fully fertile $F_1$ hybrid progeny. If no restorer gene is present in the male parent, male-sterile hybrids are obtained. Such hybrids are useful where the vegetative tissue of the cotton plant is used, e.g., for silage, but in most cases, the seeds will be deemed the most valuable portion of the crop, so fertility of the hybrids in these crops must be restored. Therefore, one aspect of the present invention concerns cotton variety 98M-2983 comprising a single gene capable of restoring male fertility in an otherwise male-sterile variety or hybrid plant. Examples of male-sterility genes and corresponding restorers which could be employed within the variety of the invention are well known to those of skill in the art of plant breeding and are disclosed in, for example, U.S. Pat. Nos. 5,530,191, 5,689,041, 5,741,684, and 5,684,242, the disclosures of which are each specifically incorporated herein by reference in their entirety.

VIII. Cotton Transformation

With the advent of molecular biological techniques that have allowed the isolation and characterization of genes that encode specific protein products, scientists in the field of plant biology developed a strong interest in engineering the genome of plants to contain and to express foreign genes, or additional, or modified versions of native or endogenous genes (perhaps driven by different promoters) to alter the traits of a plant in a specific manner. Such foreign, additional and/or modified genes are referred to herein collectively as "transgenes." The present invention, in particular embodiments, also relates to transformed versions of the claimed cotton variety 98M-2983 containing one or more transgenes.

Plant transformation involves the construction of an expression vector which will function in plant cells. Such a vector comprises DNA comprising a gene under control of or operatively linked to a regulatory element. The expression vector may contain one or more such operably linked gene/regulatory element combinations. The vector(s) may be in the form of a plasmid, and can be used, alone or in combination with other plasmids, to provide transformed cotton plants, using transformation methods as described below to incorporate transgenes into the genetic material of the cotton plant(s).

A. Expression Vectors for Cotton Transformation/Marker Genes

Expression vectors include at least one genetic marker, operably linked to a regulatory element that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from a bacterial source, which when placed under the control of plant regulatory signals confers resistance to kanamycin. Fraley et al., *Proc. Natl. Acad. Sci. U.S.A.* 80: 4803 (1983). Another commonly used selectable marker gene is the hygromycin phosphotransferase gene which confers resistance to the antibiotic hygromycin. Vanden Elzen et al., *Plant Mol. Biol.* 5: 299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86: 1216 (1988), Jones et al., *Mol. Gen. Genet.* 210: 86 (1987), Svab et al., *Plant Mol. Biol.* 14: 197 (1990), Hille et al., *Plant Mol. Biol.* 7: 171 (1986). Other selectable marker genes confer resistance to herbicides such as glyphosate, glufosinate or bromoxynil. Comai et al., *Nature* 317: 741-744 (1985), Gordon-Kamm et al., *Plant Cell* 2: 603-618 (1990) and Stalker et al., *Science* 242: 419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13: 67 (1987), Shah et al., *Science* 233: 478 (1986), Charest et al., *Plant Cell Rep.* 8: 643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5: 387 (1987), Teeri et al., *EMBO J.* 8: 343 (1989), Koncz et al., *Proc. Natl. Acad. Sci. U.S.A.* 84: 131 (1987), De Block et al., *EMBO J.* 3: 1681 (1984). Another approach to the identification of a relatively rare transformation events has been use of a gene that encodes a dominant constitutive regulator of the *Zea mays* anthocyanin pigmentation pathway. Ludwig et al., *Science* 247: 449 (1990).

Recently, in vivo methods for visualizing GUS activity that do not require destruction of plant tissue have been made available. Molecular Probes Publication 2908, Imagene Green™, p. 1-4 (1983) and Naleway et al., *J. Cell Biol.* 115: 151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

B. Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type" specific promoter primarily drives expression in certain cell types in one or more organs, for example, vascular cells in roots or leaves. An "inducible" promoter is a promoter which is under environmental control or is induced in response to chemical or hormonal stimuli. Examples of environmental conditions that may effect transcription by inducible promoters include anaerobic conditions or the presence of light. Examples of chemicals that induce expression including salicyclic acid and ABA. Tissue-specific, tissue-preferred, cell type specific, and inducible promoters constitute the class of "non-constitutive" promoters. A "constitutive" promoter is a promoter which is active under most environmental conditions and in all cells.

1. Inducible Promoters

An inducible promoter is operably linked to a gene for expression in cotton. Optionally, the inducible promoter is operably linked to a nucleotide sequence encoding a signal sequence which is operably linked to a gene for expression in cotton. With an inducible promoter the rate of transcription increases in response to an inducing agent. Any inducible promoter can be used in the instant invention. A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone.

2. Constitutive Promoters

A constitutive promoter is operably linked to a gene for expression in cotton or the constitutive promoter is operably linked to a nucleotide sequence encoding a signal sequence which is operably linked to a gene for expression in cotton. Many different constitutive promoters can be used in the present invention. Exemplary constitutive promoters include, but are not limited to, the promoters from plant viruses such as the 35S promoter from CaMV and the promoters from such genes as rice actin, maize ubiquitin, and corn H3 histone. Also, the ALS promoter, a XbaI/NcoI fragment 5' to the *Brassica napus* ALS3 structural gene (or a nucleotide sequence that has substantial sequence similarity to the XbaI/NcoI fragment) represents a particularly useful constitutive promoter.

3. Tissue-Specific or Tissue-Preferred Promoters

A tissue-specific promoter is operably linked to a gene for expression in cotton. Optionally, the tissue-specific promoter is operably linked to a nucleotide sequence encoding a signal sequence which is operably linked to a gene for expression in cotton. Plants transformed with a gene of interest operably linked to a tissue-specific promoter produce the protein product of the transgene exclusively, or preferentially, in a specific tissue. Any tissue-specific or tissue-preferred promoter can be utilized in the instant invention. Exemplary tissue-specific or tissue-preferred promoters include, but are not limited to, a seed-preferred promoter such as that from the phaseolin gene; a leaf-specific and light-induced promoter such as that from cab or rubisco; an anther-specific promoter such as that from LAT52; a pollen specific promoter such as that from Zm13 or a microspore-preferred promoter such as that from apg.

C. Signal Sequences for Targeting Proteins to Subcellular Compartments

Transport of protein produced by transgenes to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Any signal sequence known in the art is contemplated by the present invention.

D. Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods.

According to a preferred embodiment, the transgenic plant provided for commercial production of foreign protein is cotton. In another preferred embodiment, the biomass of interest is seed. For the relatively small number of transgenic plants that show higher levels of expression, a genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to:

1. Genes that Confer Resistance to Pests or Disease and that Encode:

(a) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium falvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*).

(b) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt δ-endotoxin gene. Moreover, DNA molecules encoding δ-endotoxin genes can be purchased from American Type Culture Collection (Rockville, Md.), for example, under ATCC Accession Nos. 40098, 67136, 31995 and 31998.

(c) A lectin. See, for example, the disclosure by Van Damme et al., Plant Molec. Biol. 24: 25 (1994), who disclose the nucleotide sequences of several *Clivia miniata* mannose-binding lectin genes.

(d) A vitamin-binding protein such as avidin. See PCT application US93/06487 the contents of which are hereby incorporated by. The application teaches the use of avidin and avidin homologues as larvicides against insect pests.

(e) An enzyme inhibitor, for example, a protease inhibitor or an amylase inhibitor. See, for example, Abe et al., J. Biol. Chem. 262: 16793 (1987) (nucleotide sequence of rice cysteine proteinase inhibitor), Huub et al., Plant Molec. Biol. 21: 985 (1993) (nucleotide sequence of cDNA encoding tobacco proteinase inhibitor I), and Sumitani et al., Biosci. Biotech. Biochem. 57: 1243 (1993) (nucleotide sequence of *Streptomyces nitrosporeus* α-amylase inhibitor).

(f) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(g) An insect-specific peptide or neuropeptide which, upon expression, disrupts the physiology of the affected pest. For example, see the disclosures of Regan, J. Biol. Chem. 269: 9 (1994) (expression cloning yields DNA coding for insect diuretic hormone receptor), and Pratt et al., Biochem. Biophys. Res. Comm. 163: 1243 (1989) (an allostatin is identified in *Diploptera puntata*). See also U.S. Pat. No. 5,266,317 to Tomalski et al., who disclose genes encoding insect-specific, paralytic neurotoxins.

(h) An insect-specific venom produced in nature by a snake, a wasp, etc. For example, see Pang et al., Gene 116:

165 (1992), for disclosure of heterologous expression in plants of a gene coding for a scorpion insectotoxic peptide.

(i) An enzyme responsible for an hyperaccumulation of a monterpene, a sesquiterpene, a steroid, hydroxamic acid, a phenylpropanoid derivative or another non-protein molecule with insecticidal activity.

(j) An enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene.

(k) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a corn calmodulin cDNA clone.

(l) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(m) A membrane permease, a channel former or a channel blocker. For example, see the disclosure by Jaynes et al., Plant Sci. 89: 43 (1993), of heterologous expression of a cecropin-P lytic peptide analog to render transgenic tobacco plants resistant to *Pseudomonas solanacearum*.

(n) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(o) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(p) A virus-specific antibody. See, for example, Tavladoraki et al, Nature 366: 469 (1993), who show that transgenic plants expressing recombinant antibody genes are protected from virus attack.

(q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonate. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(r) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

2. Genes that Confer Resistance to a Herbicide, for Example:

(a) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively.

(b) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phospinothricin acetyl transferase activity. Exemplary of genes conferring resistance to phenoxy proprionic acids and cyclohexones, such as sethoxydim and haloxyfop, are the Accl-S1, Accl-S2 and Accl-S3 genes described by Marshall et al., Theor. Appl. Genet. 83: 435 (1992).

(c) A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

3. Genes that Confer or Contribute to a Value-Added Trait, Such as:

(a) Modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992).

(b) Decreased phytate content:

(i) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene.

(ii) A gene could be introduced that reduces phytate content. In cotton, this, for example, could be accomplished, by cloning and then reintroducing DNA associated with the single allele which is responsible for cotton mutants characterized by low levels of phytic acid. See Raboy et al., Maydica 35: 383 (1990).

(iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus licheniformis* α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (corn endosperm starch branching enzyme II).

E. Methods for Cotton Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, inc., Boca Raton, 1993) pages 89-119.

1. *Agrobacterium*-Mediated Transformation

One method for introducing an expression vector into plants is based on the natural transformation system of *Agrobacterium*. See, for example, Horsch et al., Science 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8: 238 (1989). See also, U.S. Pat. No. 5,591,616, issued Jan. 7, 1997.

2. Direct Gene Transfer

Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm (See e.g., U.S. Pat. No. 5,550,318; U.S. Pat. No. 5,736,369, U.S. Pat. No. 5,538,880; and PCT Publication WO 95/06128). The expression vector is introduced into plant tissues with a biolistic device that accelerates the microprojectiles to speeds of 300 to 600 m/s which is sufficient to penetrate plant cell walls and membranes. Sanford et al, Part. Sci. Technol. 5: 27 (1987), Sanford, J. C., Trends Biotech. 6: 299 (1988), Klein et al., Bio/Technology 6: 559-563 (1988), Sanford, J. C., Physiol Plant 79: 206 (1990), Klein et al., Biotechnology 10: 268 (1992).

Another method for physical delivery of DNA to plants is sonication of target cells. Zhang et al., Bio/Technology 9: 996 (1991). Alternatively, liposome or spheroplast fusion have been used to introduce expression vectors into plants. Deshayes et al., EMBO J., 4: 2731 (1985), Christou et al., Proc Natl. Acad. Sci. U.S.A. 84: 3962 (1987). Direct uptake of DNA into protoplasts using $CaCl_2$ precipitation, polyvinyl alcohol or poly-L-ornithine have also been reported. Hain et al., Mol. Gen. Genet. 199: 161 (1985) and Draper et al., Plant Cell Physiol. 23: 451 (1982). Electroporation of protoplasts and whole cells and tissues have also been described. U.S. Pat. No. 5,384,253 and Donn et al. In Abstracts of VIIth International Congress on Plant Cell and Tissue Culture IAPTC, A2-38, p 53 (1990); D'Halluin et al., Plant Cell 4: 1495-1505 (1992) and Spencer et al., Plant Mol. Biol. 24: 51-61 (1994).

Other methods which have been described for the genetic transformation of cotton include, electrotransformation (U.S. Pat. No. 5,371,003) and silicon carbide fiber-mediated transformation (U.S. Pat. No. 5,302,532 and U.S. Pat. No. 5,464,765).

Following transformation of cotton target tissues, expression of the above-described selectable marker genes allows for preferential selection of transformed cells, tissues and/or plants, using regeneration and selection methods now well known in the art.

The foregoing methods for transformation would typically be used for producing transgenic cotton varieties. Transgenic cotton varieties could then be crossed, with another (non-transformed or transformed) cotton variety, to produce a transgenic hybrid cotton plant. Alternatively, a genetic trait which has been engineered into a particular cotton variety using the foregoing transformation techniques could be moved into another line using traditional backcrossing techniques that are well known in the plant breeding arts. For example, a backcrossing approach could be used to move an engineered trait from a public, non-elite line into an elite line, or from a hybrid cotton plant containing a foreign gene in its genome into a line or lines which do not contain that gene.

IX. Genetic Complements

In addition to phenotypic observations, a plant can also be described by its genotype. The genotype of a plant can be described through a genetic marker profile which can identify plants of the same variety, a related variety or be used to determine or to validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs), Isozyme Electrophoresis and Isolelectric Focusing.

Particular markers used for these purposes are not limited to the set of markers disclosed herewithin, but are envisioned to include any type of genetically stable marker and marker profile which provides a means of distinguishing varieties. In addition to being used for identification of cotton varieties, a hybrid produced through the use of 98M-2983, and identification or verification of the pedigree of progeny plants produced through the use of 98M-2983, the genetic marker profile is also useful in breeding and developing backcross conversions.

Means of performing genetic marker profiles using SSR polymorphisms are well known in the art. SSRs are genetic markers based on polymorphisms in repeated nucleotide sequences, such as microsatellites. The phrase "simple sequence repeats" or "SSR" refers to di-, tri- or tetra-nucleotide repeats within a genome. The repeat region may vary in length between genotypes while the DNA flanking the repeat is conserved such that the primers will work in a plurality of genotypes. A polymorphism between two genotypes represents repeats of different lengths between the two flanking conserved DNA sequences. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR). The PCR® detection is done by the use of two oligonucleotide primers flanking the polymorphic segment of repetitive DNA followed by DNA amplification. This step involves repeated cycles of heat denaturation of the DNA followed by annealing of the primers to their complementary sequences at low temperatures, and extension of the annealed primers with DNA polymerase. Size separation of DNA fragments on agarose or polyacrylamide gels following amplification, comprises the major part of the methodology.

DNA isolation and amplification may be performed in the present invention as follows. DNA may be extracted from plant leaf tissue using DNeasy 96 Plant Kit from Qiagen, Inc. (Valencia, Calif., U.S.A.) following an optimized September 2002 manufacturer's protocol. PCR amplifications are performed using a Quiagen HotStar™ Taq master mix in an 8 µl reaction format as follows: 2 µl DNA (5 ng/µL+6 µL of master mix). The PCR conditions are as follows: 12 mins. at 95° C., 40 cycles of 5 seconds at 94° C., 15 seconds at 55° C., 30 seconds at 72° C., 30 mins. at 72° C., followed by cooling to 4° C. Following isolation and amplification, markers can be scored by gel electrophoresis of the amplification products. Scoring of marker genotype is based on the size of the amplified fragment as measured by molecular weight (MW) rounded to the nearest integer. Multiple samples, comprised of fluorescently labeled DNA fragments may be processed in an ABI 3700 capillary-based machine and precise allele sizing and locus genotyping were done by running GeneScan and Genotyper software (PE *Applied Biosystems*, Foster City, Calif.). When comparing varieties, it is preferable if all SSR profiles are performed in the same lab. An SSR service is available to the public on a contractual basis by Paragen, Research Triangle Park, N.C. (formerly Celera AgGen of Davis, Calif.). SSR information is provided in TABLE 5.

A genetic marker profile of a variety may be predictive of the agronomic traits of a hybrid produced using that variety. For example, if a variety of known genetic marker profile and phenotype is crossed with a second variety of known genetic marker profile and phenotype it is possible to predict the phenotype of the $F_1$ hybrid based on the combined genetic marker profiles of the parent varieties. Methods for prediction of hybrid performance from genetic marker data are disclosed in U.S. Pat. No. 5,492,547, the disclosure of which is specifically incorporated herein by reference in its entirety. Such predictions may be made using any suitable laboratory-based techniques for the analysis, comparison and characterization of plant genotype.

The most widely used of these laboratory techniques are Isozyme Electrophoresis and RFLPs. Isozyme Electrophoresis is a useful tool in determining genetic composition, although it has relatively low number of available markers and the low number of allelic variants among cotton varieties. RFLPs have the advantage of revealing an exceptionally high degree of allelic variation in cotton and the number of available markers is almost limitless. The present invention provides a genetic complement of the cotton plant variety designated 98M-2983. Further provided by the invention is a hybrid genetic complement, wherein the complement is formed by the combination of a haploid genetic complement from 98M-2983 and another haploid genetic complement. Means for determining such a genetic complement are well-known in the art.

As used herein, the phrase "genetic complement" means an aggregate of nucleotide sequences, the expression of which defines the phenotype of a cotton plant or a cell or a tissue of that plant. By way of example, a cotton plant is genotyped to determine a representative sample of the inherited markers it possesses. Markers are alleles at a single locus. They are preferably inherited in codominant fashion so that the presence of both alleles at a diploid locus is readily detectable and they are free of environmental variation, i.e., their heritability is 1. This genotyping is preferably performed on at least one generation of the descendant plant for which the numerical value of the quantitative trait(s) of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus.

The SSR genetic marker profile of cotton variety 98M-2983 was determined. Because a variety is essentially homozygous at many relevant loci, a cotton variety should, in such cases, have both the alleles of one size at each locus. In contrast, a diploid genetic marker profile of a hybrid should be the sum of those parents, e.g., if one varietal parent had the allele 168 (base pairs) at a particular locus, and the other varietal parent had 172, the hybrid is. 168,172 by inference. Subsequent generations of progeny produced by selection and breeding are expected to be of genotype 168, 172, or 168,172 for that locus by inference. When the $F_1$ plant is used to produce a variety, the locus should be either 168 or 172 for that position. Surprisingly, it has been observed that in certain instances, novel SSR genotypes arise during the breeding process. For example, a genotype of 170 may be observed at a particular locus positions from the cross of parental variety with 168 and 172 at that locus. Such a novel SSR genotype may further define a variety from the parental plants from which it was derived. An SSR genetic marker profile of 98M-2983 is presented in Table 3 wherein representative measured fragment lengths of alleles are given.

TABLE 3

| Genbank Accession No. | Forward Primer Sequence 5'-3<br>Reverse Primer Sequence 5'-3' | Fragment Length |
|---|---|---|
| AF351289.1 | GTAGTCTTCTCAACTCCACTGTT<br>GGTGACATCAGTGTTGTTC | 199.94 |
| AF351289.1 | GTAGTCTTCTCAACTCCACTGTT<br>GGTGACATCAGTGTTGTTC | 232.7 |

TABLE 3-continued

| Genbank Accession No. | Forward Primer Sequence 5'-3 Reverse Primer Sequence 5'-3' | Fragment Length |
|---|---|---|
| AF351289.1 | GTAGTCTTCTCAACTCCACTGTT GGTGACATCAGTGTTGTTC | 161.04 |
| AF351340.1 | CCAAGTCAAGGTGAGTTATATG GCTCTTTGTTACTGAAATGGG | 126.26 |
| AF351348.1 | GGCGAAGAGCTACCTGTGAATGGC CCAATGGGGACTCTACATGTGGC | 184.97 |
| AF351352.1 | GATTTAAGGTCTTTGATCCG CAAGGGTTAGTAGGTGTGTATAC | 94.73 |
| AF351352.1 | GATTTAAGGTCTTTGATCCG CAAGGGTTAGTAGGTGTGTATAC | 79.26 |
| AF351390.1 | GATGCACCAGATCCTTTTATTAG GGTACATCGGAATCACAGTG | 231.06 |
| AF351453.1 | CGAGAAGATGAGATTGGAGGAG CCCTTCTGAGTTTTCTTTGG | 128.85 |
| AF351465.1 | CGAGAAGATGAGATTGGAGGAG GGTTTTCCATTCTCTTTCATTTTC | 98.47 |
| AF351466.1 | CAGAACAACACCATCAACACTCTCAG GGCAAGCAAAGCAAAACTC | 240.87 |
| AF351466.1 | CAGAACAACACCATCAACACTCTCAG GGCAAGCAAAGCAAAACTC | 247.5 |
| BNL1162 | CTGCGCAAGCGTAGGAGTT GAAAAGAGGGGAAAAGAAATGTAAAGA | 221.67 |
| AW187493.2 | TGGGTTCTTCTTCACTCTCCTCTATTC CATTGGTGCTGGTGCCTTTTGT | 118.12 |
| BNL1317 | GATTAAAACATAATAAAAATCAGCCAAATTGG CTTCCGCCACGTAAGTCCTTCATT | 93.7 |
| BNL1317 | GATTAAAACATAATAAAAATCAGCCAAATTGG CTTCCGCCACGTAAGTCCTTCATT | 115.78 |
| BNL1454 | GGAGCGAAGGAAGAGGCAGAGA CTTTCCCCTCCCTTTTCAAGTG | 96.15 |
| BNL1513 | GTGTCTTGTCAGTTTTTGGCATCC TACAGGTTCAAAGTTGATAGGGTAATCTC | 368.95 |
| BG444502.1 | TGCGGCATATGTTGCGAGGAGT CCCCAAGGAAAACACCAGCAATAAAC | 250.17 |
| BG444426.1 | TAGATTTTTATTCTTCAGTAATGGCTTTCA GATATGGTGTTTTCCGACAGTTTCTCA | 259.25 |
| BG444171.1 | TTATCACAGGCTCCAAAATCAGG TTAGCCCAGAAAACCACAATCCA | 241.9 |
| BG444171.1 | TTATCACAGGCTCCAAAATCAGG TTAGCCCAGAAAACCACAATCCA | 251.96 |
| BG444045.1 | CCCGAAATCCAAAGCCGAAGTCT GAAGGGCTGGAAAAACACGCATCT | 319.6 |
| BG444045.1 | CCCGAAATCCAAAGCCGAAGTCT GAAGGGCTGGAAAAACACGCATCT | 331.12 |
| BG442897.1 | GCAGCAGCCTCTAATATTCTACCAACTT ATCACAATCAACAACTACGCTTTCAACTG | 131.2 |
| BNL1694 | TAGCCGTTAGAACTAATTTGAAACAG TGACTAAATTAAATATTATTGGTGGATTC | 282.91 |
| BNL1694 | TAGCCGTTAGAACTAATTTGAAACAG TGACTAAATTAAATATTATTGGTGGATTC | 299.92 |
| BNL2667 | AGTCTCCCAATCAACTTCCTTCAGT TCGACAAAGACACTCCAAAAACTACT | 266.12 |

TABLE 3-continued

| Genbank Accession No. | Forward Primer Sequence 5'-3<br>Reverse Primer Sequence 5'-3' | Fragment Length |
| --- | --- | --- |
| BNL2960 | TAAGCTCTGGAGGCCAAAAA<br>CCATTTCAATTTCAAGCATACG | 150.86 |
| BNL2986 | CCTTTGCTGGGGTTAGATTTAGAGA<br>TAGCTGTTGGGGAGGGAAGGA | 220.75 |
| BNL3031 | CTGACCCTTTAAGGAGCAACC<br>AACCCCAACAATTTAGCCACTG | 286.55 |
| BNL3031 | CTGACCCTTTAAGGAGCAACC<br>AACCCCAACAATTTAGCCACTG | 316.95 |
| BNL3140 | CACCATTGTGGCAACTGAGT<br>GGAAAAGGGAAAGCCATTGT | 105 |
| BNL3144 | TGACCGCCGGCACACGA<br>AAAGGTCTAAAAGCCCACTTCCACTGAT | 233.51 |
| BNL3144 | TGACCGCCGGCACACGA<br>AAAGGTCTAAAAGCCCACTTCCACTGAT | 219.32 |
| BNL3408 | ATCCAAACCATTGCACCACT<br>GTGTACGTTGAGAAGTCATCTGC | 129.16 |
| BNL3408 | ATCCAAACCATTGCACCACT<br>GTGTACGTTGAGAAGTCATCTGC | 142.11 |
| BNL3408 | ATCCAAACCATTGCACCACT<br>GTGTACGTTGAGAAGTCATCTGC | 116.13 |
| BNL3511 | GCATTTGTTCCGGTTCTCCTCTTT<br>GACAATGATTTTTCGTTTCGGTTTTCT | 78.57 |
| BNL3530 | TTCGGGAGCAATAGAAGAGCTAGGAGTTAT<br>ATCGTGTCGCGCCACAAGGTATG | 198.93 |
| BNL3530 | TTCGGGAGCAATAGAAGAGCTAGGAGTTAT<br>ATCGTGTCGCGCCACAAGGTATG | 210.46 |
| BNL3592 | CATTTGAATTATCTATTGCTCCTAACATCT<br>TCCAATTGGGACCTCTTTAACAGTGTA | 213.27 |
| BNL3626 | TGTTTCCTTTTCCGCCATTTTCTCT<br>GTAGTGGGGTAGCCGATGGAGTAATGA | 318.95 |
| BNL3626 | TGTTTCCTTTTCCGCCATTTTCTCT<br>GTAGTGGGGTAGCCGATGGAGTAATGA | 351.31 |
| BNL3902 | GTAGAGTTTGGGGGCTGTGTATGA<br>TGAAACTAAGCCCAAGAAGACTGATT | 121.07 |
| BNL3902 | GTAGAGTTTGGGGGCTGTGTATGA<br>TGAAACTAAGCCCAAGAAGACTGATT | 112.91 |
| BNL4030 | TATCTATGTATTGCACCCTCCCTCACTTA<br>ACTTGGTCATTTGCCTTTTGCTTTTG | 308.58 |
| — | GTCGGCCGAAAAGGTGATCTAAT<br>ATGATGATATCACACCCTTCAACAAATC | 182.18 |
| — | AAGCTTCGATTGTGCTCCACTTTAC<br>ATTTGCCTTTGATCTCAACATAGTTCAG | 211.11 |
| — | GACGCGCCCGCCATCTT<br>AAGCAAATAAGCAGAACGATCCAAATAATAAT | 115.42 |
| — | GACGCGCCCGCCATCTT<br>AAGCAAATAAGCAGAACGATCCAAATAATAAT | 104.12 |
| — | TTGCAAAAAGGGGAAAACTGA<br>GGTGCATTACTCCCCTATCTATCTC | 221.7 |
| — | TTGCAAAAAGGGGAAAACTGA<br>GGTGCATTACTCCCCTATCTATCTC | 209.96 |

The present invention also provides a hybrid genetic complement formed by the combination of a haploid genetic complement of the cotton plant 98M-2983 with a haploid genetic complement of a second cotton plant. Means for combining a haploid genetic complement from the foregoing variety with another haploid genetic complement may comprise any method for producing a hybrid plant from 98M-2983. It is contemplated that such a hybrid genetic complement can be prepared using in vitro regeneration of a tissue culture of a hybrid plant of this invention.

In addition, plants and plant parts substantially benefiting from the use of 98M-2983 in their development such as 98M-2983 comprising a backcross conversion, or transgene, may be identified by having a molecular marker profile with a high percent identity to 98M-2983. Such a percent identity might be 85%, 90%, 91%, 92%, 93%, 94%, 95%, 96%, 97%, 98%, 99%, 99.5% or 99.9% identical to 98M-2983.

The SSR profile of 98M-2983 also can be used to identify derived varieties and other progeny lines developed from the use of 98M-2983, as well as cells and other plant parts thereof. Progeny plants and plant parts produced using 98M-2983 may be identified by having a molecular marker profile of at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from cotton plant 98M-2983.

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in some detail by way of illustration and example for purposes of clarity and understanding. However, it should be appreciated by those having ordinary skill in the art that certain changes and modifications such as single gene modifications and mutations, somoclonal variants, variant individuals selected from large populations of the plants of the instant variety and the like may be practiced within the scope of the invention, as limited only by the scope of the appended claims, without departing from the true concept, spirit, and scope of the invention.

What is claimed is:

1. A seed of cotton variety designated 98M-2983, a representative sample of seed having been deposited under ATCC Accession No. PTA-9770.

2. A part of the cotton seed of claim 1.

3. The seed part of claim 2, wherein the seed part is selected from the group consisting of hull, seedcoat, germ, and endosperm.

4. The seed of claim 1, further comprising a coating.

5. A homogenous composition of the cotton seed of claim 1.

6. A cotton plant produced by growing the seed of claim 1.

7. A part of the cotton plant of claim 6, selected from the group consisting of an intact plant cell, a plant protoplast, embryos, pollen, flowers, seeds, linters, fibers, pods, gossypol glands, leaves, bolls, stems, roots, root tips, and anthers.

8. Pollen of the plant of claim 6.

9. An ovule of the plant of claim 6.

10. A tissue culture of regenerable cells or protoplasts from the cotton plant of claim 6.

11. The tissue culture according to claim 10, the cells or protoplasts of the tissue culture being from a tissue selected from the group consisting of embryos, pollen, flowers, seeds, linters, fibers, pods, gossypol glands, leaves, bolls, stems, roots, root tips, and anthers.

12. A cotton plant regenerated from the tissue culture of claim 10, wherein the regenerated plant expresses all the morphological and physiological characteristics of variety 98M-2983 listed in Table 1 when grown in the same environmental conditions.

13. A cotton plant with all the physiological and morphological characteristics of cotton variety 98M-2983 listed in Table 1 when grown in the same environmental conditions, wherein the cotton plant is produced by a tissue culture process using the cotton plant of claim 6 as a starting material for the process.

14. A method for producing a seed of a cotton plant, comprising:
(a) planting seed of claim 1 in proximity to itself or to different seed from a different variety;
(b) growing plants from the seed of claim 1 under pollinating conditions; and,
(c) harvesting resultant seed from the plant of step (b).

15. A cotton seed produced by the method of claim 14.

16. The method of claim 14, further comprising pre-treating the seed of claim 1 before performing step (a).

17. The method of claim 14, further comprising treating the growing plants or soil surrounding the growing plants with an agricultural chemical.

18. A cotton plant having all the physiological and morphological characteristics of cotton variety designated 98M-2983, a representative sample of seed having been deposited under ATCC Accession No. PTA-9770, listed in Table 1 when grown in the same environmental conditions.

19. The cotton plant of claim 18, wherein the plant is male sterile.

20. The male sterile cotton plant of claim 19, wherein the plant is a cytoplasmic male sterile plant.

21. The cotton plant of claim 18, or a part thereof, wherein the plant or parts thereof has been transformed so that its genetic material contains one or more transgenes operably linked to one or more regulatory elements.

22. The cotton plant according to claim 21, wherein said one or more transgenes comprises a gene conferring upon said cotton plant tolerance to a herbicide.

23. The cotton plant according to claim 22, wherein said herbicide is glyphosate, gluphosinate, sulfonylurea, imidazolinone, a hydroxyphenylpyruvate dioxygenase inhibitor or a protoporphyrinogen oxidase inhibitor.

24. The cotton plant according to claim 21, wherein the one or more transgenes comprises a gene conferring upon said cotton plant insect resistance, disease resistance or virus resistance.

25. The cotton plant according to claim 24, wherein the gene conferring upon the cotton plant insect resistance is a *Bacillus thuringiensis* gene.

26. The seed of the plant according to claim 21.

27. A method producing a cotton plant, comprising: crossing cotton variety plant 98M-2983, representative seed of the variety having been deposited under ATCC Accession No. PTA-9770 with another different cotton plant to yield F1 cotton seed.

28. The method of claim 27, wherein the other, different cotton plant is a cotton variety.

29. The method of claim 27, further comprising: growing the F1 cotton seed under self-pollinating or sib-pollinating conditions for about 5 to about 7 generations; and harvesting the resultant seed.

30. The method of claim 27, further comprising selecting plants obtained from growing at least one generation of the F1 cotton seed for a desirable trait.

31. The method of claim 27, wherein the plants of the other cotton variety comprise a desired trait selected from the group consisting of male sterility, herbicide resistance, insect resistance, and resistance to bacterial, fungal and viral disease.

32. The method of claim 27, further comprising using genetic markers to compare a genetic complement of a progeny plant with a genetic complement of 98M-2983.

33. The method of claim 27, further comprising using direct or indirect selection to determine whether the desired trait is present in a progeny plant.

34. A method of introducing a desired trait into cotton variety 98M-2983, a representative sample of seed having been deposited under ATCC Accession No. PTA-9770, comprising:
(a) crossing 98M-2983 plants with plants of another cotton variety that comprise a desired trait to produce F1 progeny plants;
(b) selecting F1 progeny plants that have the desired trait;
(c) crossing selected progeny plants with 98M-2983 plants to produce backcross progeny plants;
(d) selecting for backcross progeny plants that comprise the desired trait and physiological and morphological characteristics of cotton variety 98M-2983; and, (e) performing steps (c) and (d) one or more times in succession to produce the selected backcross progeny plants that comprise the desired trait and all of the physiological and morphological characteristics of cotton variety 98M-2983 listed in Table 1 when grown in the same environmental conditions.

35. A method for producing a cotton plant, comprising:
(a) crossing the cotton plant of claim 6 with another different cotton plant to produce a diploid or progeny plant;
(b) generating a haploid progeny plant from the diploid progeny plant;
(c) generating a diploid plant from the haploid progeny plant; and,
(d) selecting the diploid cotton plant of step (c).

36. The method of claim 35, wherein the haploid progeny plant is generated by culturing a haploid explant from the diploid progeny plant of step (a).

37. The method of claim 35, wherein the haploid progeny plant is generated by crossing the progeny plant produced in step (a) with another, different plant that induces haploid cotton plants.

38. The method of claim 37, wherein the other, different plant is a cotton plant that comprises a haploid-inducing gene.

39. The method of claim 35, wherein the diploid plant of step c) is generated by subjecting the haploid progeny plant to a treatment which induces chromosome doubling in the cultured explant.

40. The method of claim 35, wherein the diploid plant of step c) is generated by self pollinating the haploid progeny plant.

41. A method for producing a cotton plant, comprising:
(a) inducing a mutation in the cotton plant of claim 6; and,
(b) selecting a mutated cotton plant.

42. The method of claim 41, wherein the mutation is artificially induced by a method selected from the group consisting of elevated temperature, long-terra seed storage, tissue culture conditions, radiation, and chemical mutagenesis.

43. A method for producing a cotton plant variety, comprising:
(a) growing first generation hybrid cotton plants having a cotton variety 98M-2983, a representative sample of seed of variety 98M-2983 having been deposited under ATCC Accession NO. PTA-9770, as a parent cotton plant;
(b) inbreeding the first generation hybrid cotton plants or crossing the first generation hybrid cotton plants with different cotton plants to yield progeny cotton seed;
(c) growing the progeny cotton seed of step b) to yield further progeny cotton seed;
(d) repeating the inbreeding or the crossing and the growing steps of b) and c) from about 0 to about 7 times to generate a cotton varietal plant.

44. A method for producing cotton variety 98M-2983, representative seed of the variety having been deposited under ATCC Accession No. PTA-9770, comprising;
(a) planting a collection of seed comprising seed of a hybrid, one of whose parents is 98M-2983, the collection of seed also comprising seed of 98M-2983;
(b) growing plants from the collection of seed;
(c) identifying plants of variety 98M-2983;
d) controlling pollination in a manner which preserves the homozygosity of the plants of variety 98M-2983; and,
(e) harvesting resultant seed of variety 98M-2983.

45. The method of claim 44, wherein step (c) comprises identifying plants with decreased vigor.

46. A method for producing a varietal cotton plant comprising:
sib-pollinating plants obtained by growing the harvested resultant seed of step (e) of claim 44.

47. A method for producing a varietal cotton plant comprising:
crossing 98M-2983 cotton plants with cotton plants obtained by growing the hybrid seed of step (a) of claim 44.

48. A method for producing a hybrid cotton seed comprising crossing a first varietal parent cotton plant with a second varietal parent cotton plant and harvesting resultant hybrid cotton seed, wherein the first varietal cotton plant or the second varietal cotton plant is the cotton plant of claim 6.

49. A method for producing a hybrid cotton seed comprising the steps of:
(a) planting in pollinating proximity seeds of a first and a second varietal parent cotton plant, wherein the first varietal cotton plant or the second varietal cotton plant is the cotton plant of claim 6;
(b) cultivating the seeds of the first and the second varietal cotton plants into plants that bear flowers;
(c) controlling the male fertility of the first or the second varietal cotton plant to produce a male sterile cotton plant;
(d) allowing cross-pollination to occur between the first and second varietal cotton plants; and,
(e) harvesting a hybrid seed produced on the male sterile cotton plant.

50. The method according to claim 49, wherein the cotton plant of claim 6 is a female parent.

51. The method according to claim 49, wherein the cotton plant of claim 6 is a male parent.

52. A hybrid cotton seed produced by the method of claim 49.

53. A hybrid cotton plant produced by growing the hybrid cotton seed of claim 52.

54. A tissue culture of regenerable cells from the hybrid cotton plant of claim 53.

55. An F1 hybrid cotton seed produced by crossing the cotton plant according to claim 6 with another, different plant.

56. A hybrid cotton plant produced by growing the hybrid cotton seed of claim 55.

57. The cotton seed of claim 55, wherein the other, different plant is not a member of the hirsutum species.

58. The cotton seed of claim 55, wherein the other, different plant is a member of the barbadense species.

59. The cotton seed of claim 55, wherein the other, different plant is a member of a genus *Gossypium*.

60. The cotton seed of claim 55, wherein the other, different plant is a member of the family Malvaceae.

61. A method for producing a 98M-2983-derived cotton plant, comprising:
(a) crossing cotton variety 98M-2983, representative seed of the variety having been deposited under ATCC Accession No. PTA-9770, with a second cotton plant to yield progeny cotton seed; and
(b) growing said progeny cotton seed, under plant growth conditions, to yield said 98M-2983-derived cotton plant.

62. The 98M-2983-derived cotton plant produced by the method according to claim 61, wherein said plant has all the physiological and morphological characteristics of cotton variety 98M-2983 listed in Table 1 when grown in the same environmental conditions.

63. The method of claim 61, further comprising:
(c) crossing the 98M-2983-derived cotton plant with itself or another cotton plant to yield additional 98M-2983-derived progeny cotton seed;

(d) growing the progeny cotton seed of step c) under plant growth conditions, to yield additional 98M-2983-derived cotton plants; and (e) repeating the crossing and growing steps of c) and d) from 0 to 7 times to generate further 98M-2983-derived cotton plants.

64. The method of claim 61, still further comprising utilizing plant tissue culture methods and/or haploid breeding to derive progeny of said 98M-2983-derived cotton plant.

65. A method for regenerating a cotton plant comprising the steps of:
(a) culturing an explant comprising a tissue selected from the group consisting of a tissue obtained from cotton plant variety 98M-2983 representative seed having been deposited under ATCC Accession No. PTA-9770, an immature tissue obtained from a hybrid cotton plant having 98M-2983 as a parent, and a 98M-2983-derived cotton plant; and,
(b) initiating regeneration.

66. The method of claim 65, wherein the explant is an immature tissue.

67. A method for producing a male sterile 98M-2983 cotton plant, comprising:
(a) crossing the cotton plant of claim 6, with a cytoplasmic male sterile cotton plant which generates haploids;
(b) identifying and doubling haploid plants; and,
(c) crossing the plants of step (b) with the cotton plant 98M-2983 to produce a male sterile 98M-2983 cotton plant.

68. A cotton plant, or a part thereof, resulting from the transformation of a cotton variety designated 98M-2983, or a part thereof, a representative sample of seed having been deposited under ATCC Accession No. PTA-9770, so that the genetic material of said plant contains one or more transgenes operably linked to one or more regulatory elements, wherein said plant has all the physiological and morphological characteristics of cotton variety 98M-2983 listed in Table 1 when grown in the same environmental conditions.

69. A method for producing a cotton plant that contains in its genetic material one or more transgenes, comprising crossing the cotton plant of claim 21 with either a second plant of another cotton variety, or a non-transformed cotton plant of the variety 98M-2983, so that the genetic material of the progeny that result from the cross contains the transgene(s) operably linked to a regulatory element.

70. A cotton plant, or parts thereof, produced by the method of claim 69, wherein said plant has all the physiological and morphological characteristics of cotton variety 98M-2983 listed in Table 1 when grown in the same environmental conditions.

71. A single cross first generation hybrid cotton plant, or a part thereof, comprising two sets of alleles, wherein one set of the alleles is the same as the plant of claim 6 at all of the SSR loci listed in Table 3.

72. An inbred cotton plant variety having an SSR genetic marker profile comprising all of the genetic markers of Table 3, wherein said plant has all the physiological and morphological characteristics of cotton variety 98M-2983 listed in Table 1 when grown in the same environmental conditions.

73. A method for producing a population of 98M-2983 progeny cotton plants comprising:
(a) obtaining a first generation progeny cotton seed having the plant of claim 6 as a parent;
(b) growing the first generation progeny cotton seed to produce F1 generation cotton plants and obtaining self or sib pollinated seed from the F1 generation cotton plants comprising 98M-2983 progeny cotton plants, wherein the 98M-2983 progeny cotton plants comprise at least one physiological or morphological characteristic from the plant of claim 6; and,
(c) producing successive filial generations to obtain a population of 98M-2983 progeny cotton plants, comprising at least one physiological or morphological characteristic from the plant of claim 6.

74. A cotton plant part from a cotton plant, said cotton plant having all the physiological and morphological characteristics of cotton variety designated 98M-2983, a representative sample of seed having been deposited under ATCC Accession No. PTA-9770, listed in Table 1 when grown in the same environmental conditions.

\* \* \* \* \*

SEQUENCE LISTING

<160> NUMBER OF SEQ ID NOS: 53

<210> SEQ ID NO 1
<211> LENGTH: 42
<212> TYPE: DNA
<213> ORGANISM: Gossypium hirsutum

<400> SEQUENCE: 1
gtagtcttct caactccact gttggtgaca tcagtgttgt tc                      42

<210> SEQ ID NO 2
<211> LENGTH: 42
<212> TYPE: DNA
<213> ORGANISM: Gossypium hirsutum

<400> SEQUENCE: 2
gtagtcttct caactccact gttggtgaca tcagtgttgt tc                      42

<210> SEQ ID NO 3
<211> LENGTH: 42
<212> TYPE: DNA
<213> ORGANISM: Gossypium hirsutum

<400> SEQUENCE: 3
gtagtcttct caactccact gttggtgaca tcagtgttgt tc                      42

<210> SEQ ID NO 4
<211> LENGTH: 43
<212> TYPE: DNA
<213> ORGANISM: Gossypium hirsutum

<400> SEQUENCE: 4
ccaagtcaag gtgagttata tggctctttg ttactgaaat ggg                     43

<210> SEQ ID NO 5
<211> LENGTH: 47
<212> TYPE: DNA
<213> ORGANISM: Gossypium hirsutum

<400> SEQUENCE: 5
ggcgaagagc tacctgtgaa tggcccaatg gggactctac atgtggc                 47

<210> SEQ ID NO 6
<211> LENGTH: 43
<212> TYPE: DNA
<213> ORGANISM: Gossypium hirsutum

<400> SEQUENCE: 6
gatttaaggt ctttgatccg caagggttag taggtgtgta tac                43

<210> SEQ ID NO 7
<211> LENGTH: 43
<212> TYPE: DNA
<213> ORGANISM: Gossypium hirsutum

<400> SEQUENCE: 7
gatttaaggt ctttgatccg caagggttag taggtgtgta tac                43

<210> SEQ ID NO 8
<211> LENGTH: 43
<212> TYPE: DNA
<213> ORGANISM: Gossypium hirsutum

<400> SEQUENCE: 8
gatgcaccag atccttttat tagggtacat cggaatcaca gtg                43

<210> SEQ ID NO 9
<211> LENGTH: 42
<212> TYPE: DNA
<213> ORGANISM: Gossypium hirsutum

<400> SEQUENCE: 9
cgagaagatg agattggagg agcccttctg agttttcttt gg                 42

<210> SEQ ID NO 10
<211> LENGTH: 46
<212> TYPE: DNA
<213> ORGANISM: Gossypium hirsutum

<400> SEQUENCE: 10
cgagaagatg agattggagg agggttttcc attctctttc attttc             46

<210> SEQ ID NO 11
<211> LENGTH: 45
<212> TYPE: DNA
<213> ORGANISM: Gossypium hirsutum

<400> SEQUENCE: 11
cagaacaaca ccatcaacac tctcagggca agcaaagcaa aactc              45

<210> SEQ ID NO 12
<211> LENGTH: 45
<212> TYPE: DNA
<213> ORGANISM: Gossypium hirsutum

<400> SEQUENCE: 12
cagaacaaca ccatcaacac tctcagggca agcaaagcaa aactc              45

<210> SEQ ID NO 13
<211> LENGTH: 46
<212> TYPE: DNA
<213> ORGANISM: Gossypium hirsutum

<400> SEQUENCE: 13
ctgcgcaagc gtaggagttg aaaagagggg aaaagaaatg taaaga                    46

<210> SEQ ID NO 14
<211> LENGTH: 49
<212> TYPE: DNA
<213> ORGANISM: Gossypium hirsutum

<400> SEQUENCE: 14
tgggttcttc ttcactctcc tctattccat tggtgctggt gccttttgt                 49

<210> SEQ ID NO 15
<211> LENGTH: 56
<212> TYPE: DNA
<213> ORGANISM: Gossypium hirsutum

<400> SEQUENCE: 15
gattaaaaca taataaaaat cagccaaatt ggcttccgcc acgtaagtcc ttcatt         56

<210> SEQ ID NO 16
<211> LENGTH: 56
<212> TYPE: DNA
<213> ORGANISM: Gossypium hirsutum

<400> SEQUENCE: 16
gattaaaaca taataaaaat cagccaaatt ggcttccgcc acgtaagtcc ttcatt         56

<210> SEQ ID NO 17
<211> LENGTH: 44
<212> TYPE: DNA
<213> ORGANISM: Gossypium hirsutum

<400> SEQUENCE: 17
ggagcgaagg aagaggcaga gactttcccc tccctttca agtg                      44

<210> SEQ ID NO 18
<211> LENGTH: 53
<212> TYPE: DNA
<213> ORGANISM: Gossypium hirsutum

<400> SEQUENCE: 18
gtgtcttgtc agttttggc atcctacagg ttcaaagttg atagggtaat ctc            53

<210> SEQ ID NO 19
<211> LENGTH: 48
<212> TYPE: DNA
<213> ORGANISM: Gossypium hirsutum

<400> SEQUENCE: 19
tgcggcatat gttgcgagga gtccccaagg aaaacaccag caataaac                 48

<210> SEQ ID NO 20
<211> LENGTH: 57
<212> TYPE: DNA
<213> ORGANISM: Gossypium hirsutum

<400> SEQUENCE: 20
tagattttta ttcttcagta atggctttca gatatggtgt tttccgacag tttctca       57

<210> SEQ ID NO 21
<211> LENGTH: 46
<212> TYPE: DNA
<213> ORGANISM: Gossypium hirsutum

<400> SEQUENCE: 21
ttatcacagg ctccaaaatc aggttagccc agaaaaccac aatcca         46

<210> SEQ ID NO 22
<211> LENGTH: 46
<212> TYPE: DNA
<213> ORGANISM: Gossypium hirsutum

<400> SEQUENCE: 22
ttatcacagg ctccaaaatc aggttagccc agaaaaccac aatcca         46

<210> SEQ ID NO 23
<211> LENGTH: 47
<212> TYPE: DNA
<213> ORGANISM: Gossypium hirsutum

<400> SEQUENCE: 23
cccgaaatcc aaagccgaag tctgaagggc tggaaaaaca cgcatct        47

<210> SEQ ID NO 24
<211> LENGTH: 47
<212> TYPE: DNA
<213> ORGANISM: Gossypium hirsutum

<400> SEQUENCE: 24
cccgaaatcc aaagccgaag tctgaagggc tggaaaaaca cgcatct        47

<210> SEQ ID NO 25
<211> LENGTH: 57
<212> TYPE: DNA
<213> ORGANISM: Gossypium hirsutum

<400> SEQUENCE: 25
gcagcagcct ctaatattct accaacttat cacaatcaac aactacgctt tcaactg    57

<210> SEQ ID NO 26
<211> LENGTH: 55
<212> TYPE: DNA
<213> ORGANISM: Gossypium hirsutum

<400> SEQUENCE: 26
tagccgttag aactaatttg aaacagtgac taaattaaat attattggtg gattc      55

<210> SEQ ID NO 27
<211> LENGTH: 55
<212> TYPE: DNA
<213> ORGANISM: Gossypium hirsutum

<400> SEQUENCE: 27
tagccgttag aactaatttg aaacagtgac taaattaaat attattggtg gattc      55

<210> SEQ ID NO 28
<211> LENGTH: 51
<212> TYPE: DNA
<213> ORGANISM: Gossypium hirsutum

<400> SEQUENCE: 28
agtctcccaa tcaacttcct tcagttcgac aaagacactc caaaaactac t          51

<210> SEQ ID NO 29
<211> LENGTH: 42
<212> TYPE: DNA
<213> ORGANISM: Gossypium hirsutum

<400> SEQUENCE: 29
taagctctgg aggccaaaaa ccatttcaat ttcaagcata cg                42

<210> SEQ ID NO 30
<211> LENGTH: 46
<212> TYPE: DNA
<213> ORGANISM: Gossypium hirsutum

<400> SEQUENCE: 30
cctttgctgg ggttagattt agagatagct gttggggagg gaagga           46

<210> SEQ ID NO 31
<211> LENGTH: 43
<212> TYPE: DNA
<213> ORGANISM: Gossypium hirsutum

<400> SEQUENCE: 31
ctgacccttt aaggagcaac caaccccaac aatttagcca ctg               43

<210> SEQ ID NO 32
<211> LENGTH: 43
<212> TYPE: DNA
<213> ORGANISM: Gossypium hirsutum

<400> SEQUENCE: 32
ctgacccttt aaggagcaac caaccccaac aatttagcca ctg               43

<210> SEQ ID NO 33
<211> LENGTH: 40
<212> TYPE: DNA
<213> ORGANISM: Gossypium hirsutum

<400> SEQUENCE: 33
caccattgtg gcaactgagt ggaaaaggga aagccattgt                    40

<210> SEQ ID NO 34
<211> LENGTH: 45
<212> TYPE: DNA
<213> ORGANISM: Gossypium hirsutum

<400> SEQUENCE: 34
tgaccgccgg cacacgaaaa ggtctaaaag cccacttcca ctgat             45

<210> SEQ ID NO 35
<211> LENGTH: 45
<212> TYPE: DNA
<213> ORGANISM: Gossypium hirsutum

<400> SEQUENCE: 35
tgaccgccgg cacacgaaaa ggtctaaaag cccacttcca ctgat             45

<210> SEQ ID NO 36
<211> LENGTH: 43
<212> TYPE: DNA
<213> ORGANISM: Gossypium hirsutum

<400> SEQUENCE: 36
atccaaacca ttgcaccact gtgtacgttg agaagtcatc tgc               43

<210> SEQ ID NO 37
<211> LENGTH: 43
<212> TYPE: DNA
<213> ORGANISM: Gossypium hirsutum

```
<400> SEQUENCE: 37
atccaaacca ttgcaccact gtgtacgttg agaagtcatc tgc                              43

<210> SEQ ID NO 38
<211> LENGTH: 43
<212> TYPE: DNA
<213> ORGANISM: Gossypium hirsutum

<400> SEQUENCE: 38
atccaaacca ttgcaccact gtgtacgttg agaagtcatc tgc                              43

<210> SEQ ID NO 39
<211> LENGTH: 51
<212> TYPE: DNA
<213> ORGANISM: Gossypium hirsutum

<400> SEQUENCE: 39
gcatttgttc cggttctcct ctttgacaat gattttttcgt ttcggttttc t                    51

<210> SEQ ID NO 40
<211> LENGTH: 53
<212> TYPE: DNA
<213> ORGANISM: Gossypium hirsutum

<400> SEQUENCE: 40
ttcgggagca atagaagagc taggagttat atcgtgtcgc gccacaaggt atg                   53

<210> SEQ ID NO 41
<211> LENGTH: 53
<212> TYPE: DNA
<213> ORGANISM: Gossypium hirsutum

<400> SEQUENCE: 41
ttcgggagca atagaagagc taggagttat atcgtgtcgc gccacaaggt atg                   53

<210> SEQ ID NO 42
<211> LENGTH: 57
<212> TYPE: DNA
<213> ORGANISM: Gossypium hirsutum

<400> SEQUENCE: 42
catttgaatt atctattgct cctaacatct tccaattggg acctctttaa cagtgta              57

<210> SEQ ID NO 43
<211> LENGTH: 52
<212> TYPE: DNA
<213> ORGANISM: Gossypium hirsutum

<400> SEQUENCE: 43
tgtttccttt tccgccattt tctctgtagt ggggtagccg atggagtaat ga                    52

<210> SEQ ID NO 44
<211> LENGTH: 52
<212> TYPE: DNA
<213> ORGANISM: Gossypium hirsutum

<400> SEQUENCE: 44
tgtttccttt tccgccattt tctctgtagt ggggtagccg atggagtaat ga                    52

<210> SEQ ID NO 45
<211> LENGTH: 50
<212> TYPE: DNA
```

<213> ORGANISM: Gossypium hirsutum

<400> SEQUENCE: 45
gtagagtttg ggggctgtgt atgatgaaac taagcccaag aagactgatt   50

<210> SEQ ID NO 46
<211> LENGTH: 50
<212> TYPE: DNA
<213> ORGANISM: Gossypium hirsutum

<400> SEQUENCE: 46
gtagagtttg ggggctgtgt atgatgaaac taagcccaag aagactgatt   50

<210> SEQ ID NO 47
<211> LENGTH: 55
<212> TYPE: DNA
<213> ORGANISM: Gossypium hirsutum

<400> SEQUENCE: 47
tatctatgta ttgcaccctc cctcacttaa cttggtcatt tgccttttgc ttttg   55

<210> SEQ ID NO 48
<211> LENGTH: 51
<212> TYPE: DNA
<213> ORGANISM: Gossypium hirsutum

<400> SEQUENCE: 48
gtcggccgaa aaggtgatct aatatgatga tatcacaccc ttcaacaaat c   51

<210> SEQ ID NO 49
<211> LENGTH: 53
<212> TYPE: DNA
<213> ORGANISM: Gossypium hirsutum

<400> SEQUENCE: 49
aagcttcgat tgtgctccac tttacatttg cctttgatct caacatagtt cag   53

<210> SEQ ID NO 50
<211> LENGTH: 49
<212> TYPE: DNA
<213> ORGANISM: Gossypium hirsutum

<400> SEQUENCE: 50
gacgcgcccg ccatcttaag caaataagca gaacgatcca aataataat   49

<210> SEQ ID NO 51
<211> LENGTH: 49
<212> TYPE: DNA
<213> ORGANISM: Gossypium hirsutum

<400> SEQUENCE: 51
gacgcgcccg ccatcttaag caaataagca gaacgatcca aataataat   49

<210> SEQ ID NO 52
<211> LENGTH: 46
<212> TYPE: DNA
<213> ORGANISM: Gossypium hirsutum

<400> SEQUENCE: 52
ttgcaaaaag gggaaaactg aggtgcatta ctccctatc tatctc   46

<210> SEQ ID NO 53
<211> LENGTH: 46

-continued

```
<212> TYPE: DNA
<213> ORGANISM: Gossypium hirsutum

<400> SEQUENCE: 53
ttgcaaaaag gggaaaactg aggtgcatta ctcccctatc tatctc                46
```